(12) United States Patent
Cheng et al.

(10) Patent No.: US 11,793,816 B2
(45) Date of Patent: Oct. 24, 2023

(54) METHODS FOR ENHANCING CYTOTOXIC CANCER THERAPY THROUGH INHIBITION OF ATG4B

(71) Applicant: Northwestern University, Evanston, IL (US)

(72) Inventors: Shi-Yuan Cheng, Glenview, IL (US); Bo Hu, Glenview, IL (US); Tianzhi Huang, Chicago, IL (US)

(73) Assignee: Northwestern University, Evanston, IL (US)

( * ) Notice: Subject to any disclaimer, the term of this patent is extended or adjusted under 35 U.S.C. 154(b) by 211 days.

(21) Appl. No.: 17/017,351

(22) Filed: Sep. 10, 2020

(65) Prior Publication Data
US 2021/0069202 A1    Mar. 11, 2021

Related U.S. Application Data

(60) Provisional application No. 62/898,504, filed on Sep. 10, 2019.

(51) Int. Cl.

| | | |
|---|---|---|
| A61K 31/5377 | (2006.01) | |
| A61K 31/444 | (2006.01) | |
| A61K 31/427 | (2006.01) | |
| A61K 31/47 | (2006.01) | |
| A61K 31/519 | (2006.01) | |
| A61P 35/00 | (2006.01) | |
| A61K 31/53 | (2006.01) | |
| A61K 31/436 | (2006.01) | |
| A61K 31/495 | (2006.01) | |
| A61K 45/06 | (2006.01) | |
| A61K 31/437 | (2006.01) | |

(52) U.S. Cl.
CPC ........ *A61K 31/5377* (2013.01); *A61K 31/427* (2013.01); *A61K 31/436* (2013.01); *A61K 31/437* (2013.01); *A61K 31/444* (2013.01); *A61K 31/47* (2013.01); *A61K 31/495* (2013.01); *A61K 31/519* (2013.01); *A61K 31/53* (2013.01); *A61K 45/06* (2013.01); *A61P 35/00* (2018.01)

(58) Field of Classification Search
CPC ............ A61K 31/4404; A61K 31/4184; A61K 31/47; A61P 35/00
See application file for complete search history.

(56) References Cited

U.S. PATENT DOCUMENTS

| | | |
|---|---|---|
| 8,554,841 B2 | 10/2013 | Kurata et al. |
| 2010/0285012 A1 | 11/2010 | Dunn |
| 2019/0183860 A1* | 6/2019 | Yang .................. A61K 31/4745 |

FOREIGN PATENT DOCUMENTS

WO   WO-2018096088 A1 *  5/2018  ............... A61P 35/00

OTHER PUBLICATIONS

Xu et al (Medicine vol. 97 p. e12912 published 2018). (Year: 2018).*
Huang (Cancer Cell. vol. 32 pp. 840-855 published Dec. 11, 2017). (Year: 2017).*
Buccarelli (Cell Death and Disease vol. 9:841 p. 1-17 published 2018) (Year: 2018).*
Akin, D., et al. "A novel ATG4B antagonist inhibits autophagy and has a negative impact on osteosarcoma tumors." Autophagy 10.11 (2014): 2021-2035.
Bortnik, S., et al. (2016). Identification of breast cancer cell subtypes sensitive to ATG4B inhibition. Oncotarget 7, 66970-66988.
Bosc et al., A new quinolone-based chemical probe inhibits the autophagy-related cysteine protease ATG4B, Scientific Reports (2018) 8:11653, 1-17.
Cabrera, S., et al. (2013). ATG4B/autophagin-1 regulates intestinal homeostasis and protects mice from experimental colitis. Autophagy 9, 1188-1200.
Huang, T., et al. "MST4 phosphorylation of ATG4B regulates autophagic activity, tumorigenicity, and radioresistance in glioblastoma." Cancer cell 32.6 (2017): 840-855.
Kuang, E., et al. (2012). Regulation of ATG4B stability by RNF5 limits basal levels of autophagy and influences susceptibility to bacterial infection. PLoS Genet. 8, e1003007.
Li, M., et al. (2012). A high-throughput FRET-based assay for determination of Atg4 activity. Autophagy 8, 401-412.
Li, M., et al. (2011). Kinetics comparisons of mammalian Atg4 homologues indicate selective preferences toward diverse Atg8 substrates. The Journal of biological chemistry 286, 7327-7338.
Liu, P. F., et al. (2014). ATG4B promotes colorectal cancer growth independent of autophagic flux. Autophagy 10, 1454-1465.
Mizushima, N., et al. (2011). The role of Atg proteins in autophagosome formation. Annu. Rev. Cell Dev. Biol. 27, 107-132.
Read, R., et al. (2011). Histopathological and neurological features of Atg4b knockout mice. Vet. Pathol. 48, 486-494.
Rothe, K., et al. (2014). The core autophagy protein ATG4B is a potential biomarker and therapeutic target in CML stem/progenitor cells. Blood 123, 3622-3634.
Tanida et al., "HsAtg4B/HsApg4B/autophagin-1 cleaves the carboxyl termini of three human Atg8 homologues and delipidates microtubule-associated protein light chain 3- and GABAA receptor-associated protein-phospholipid conjugates," J. Biol. Chem. 279:36268-36276 (2004).
Yang, Z., et al. (2015). ATG4B (Autophagin-1) phosphorylation modulates autophagy. J. Biol. Chem. 290, 26549-26561.
Zhang, L., et al. (2016). Unraveling the roles of Atg4 proteases from autophagy modulation to targeted cancer therapy. Cancer Lett. 373, 19-26.

* cited by examiner

*Primary Examiner* — Theodore R. Howell
*Assistant Examiner* — George W Kosturko
(74) *Attorney, Agent, or Firm* — QUARLES & BRADY LLP

(57) ABSTRACT

Disclosed are methods and compositions for treating cell proliferative diseases and disorders such as cancers. Particularly disclosed are methods and composition for treating cancers such as glioblastoma by administering a therapeutic agent that inhibits the biological activity of the autophagy related 4B cysteine peptidase (ATG4B) protein in conjunction with additional therapeutic agents or treatments.

7 Claims, 21 Drawing Sheets

Specification includes a Sequence Listing.

A

PK Parameters Summary

| Dose Level (mg/kg) | Rsq | T1/2 (hr) | Tmax (hr) | Cmax (ng/ml) | Cmax (μM) | AUCall (hr*ng/ml) |
|---|---|---|---|---|---|---|
| 10 | 0.9544 | 2.0 | 0.5 | 563 | 2.6 | 2135 |
| 50 | 0.9967 | 4.2 | 0.5 | 7137 | 33 | 57248 |

Figure 1

METHODS FOR ENHANCING CYTOTOXIC CANCER THERAPY THROUGH INHIBITION OF ATG4B

CROSS-REFERENCE TO RELATED PATENT APPLICATIONS

This application claims the benefit of priority under 35 U.S.C. § 119(e) to U.S. Provisional Application No. 62/898,504, filed on Sep. 10, 2019, the content of which is incorporated by reference in its entirety.

STATEMENT REGARDING FEDERALLY SPONSORED RESEARCH OR DEVELOPMENT

This invention was made with government support under CA221747 and NS095634 awarded by the National Institutes of Health. The government has certain rights in the invention.

REFERENCE TO A SEQUENCE LISTING SUBMITTED VIA EFS-WEB

The content of the ASCII text file of the sequence listing named "702581_01595_ST25.txt" which is 15 kb in size was created on Sep. 3, 2020 and electronically submitted via EFS-Web herewith the application is incorporated herein by reference in its entirety.

BACKGROUND

The invention relates to methods and compositions for treating cell proliferative diseases and disorders such as cancers. In particular, the invention relates to methods and composition for treating cancers such as glioblastoma by administering a therapeutic agent that inhibits the biological activity of the autophagy related 4B cysteine peptidase (ATG4B) protein in conjunction with additional therapeutic agents or treatments.

Autophagy is an evolutionarily conserved process that maintains control of intracellular components through lysosome-mediated degradation. This provides a means to conserve energy, particularly in response to intrinsic and extrinsic stresses [25,28]. Upon autophagy initiation, more than 30 proteins, including autophagy-related proteins, orchestrate a multistep autophagic process that involves membrane remodeling and vesicular trafficking in four different stages: initiation/nucleation, elongation, maturation, and lysosome reformation [5,7]. At the first step, phosphatidylinositol triphosphate production by the class III phosphatidylinositol 3-kinase (PtdIns3K) in a complex with BECN1 is required for the biogenesis of autophagosome formation [15]. Next, the double-membrane elongation of the phagophore (the autophagosome precursor) involves 2 sequential ubiquitin-like conjugation steps: one involving ATG12 (autophagy related 12)-ATG5 and the other involving MAP1LC3-II/LC3-II (microtubule associated protein 1 light chain 3-II) in mammals [27]. The latter process is mediated by ATG4B (autophagy related 4B cysteine peptidase), which cleaves the precursor form of LC3 (pro-LC3). This event reveals a C-terminal glycine residue for conjugation with membrane-bound phosphatidylethanolamine, resulting an insertion of LC3-II into elongating autophagic membranes. This process is reversible because ATG4B also removes phosphatidylethanolamine from LC3-II and recycles LC3 [14,35]. LC3-II present on the inner surface of the phagophore membrane is bound with the autophagic receptor molecule SQSTM1/p62 (sequestosome 1), which sequesters ubiquitinated cargo via its ubiquitin association (UBA) domain and delivers those cargos through its LC3-interacting region [18].

In cellular and tissue repair processes, autophagy principally serves as a protective mechanism against stresses and diverse pathologies including cancer [19]. However, in advanced cancers, autophagy-mediated intracellular catabolism is co-opted to support tumor's increasing demands for energy and resources needed for growth and survival from treatments [3,34]. Cancer therapies such as irradiation and chemotherapy, especially treatment with alkylating agents, induce autophagy [17,21]. Some cancers utilize autophagy as an escape mechanism of cell survival in response to cytotoxic therapies including irradiation and treatment with alkylating agents, which are standard first-line treatments for many cancers [16,34]. Therefore, the present inventors investigated whether autophage inhibitors can be administered to treat cancer and enhance the cytotoxicity of irradiation and chemotherapy.

SUMMARY

Disclosed are methods and compositions for treating cell proliferative diseases and disorders such as cancers. Particularly disclosed are methods and composition for treating cancers such as glioblastoma by administering a therapeutic agent that inhibits the biological activity of the autophagy related 4B cysteine peptidase (ATG4B) protein in conjunction with additional therapeutic agents or treatments in order to enhance cytotoxicity.

Figure 3:
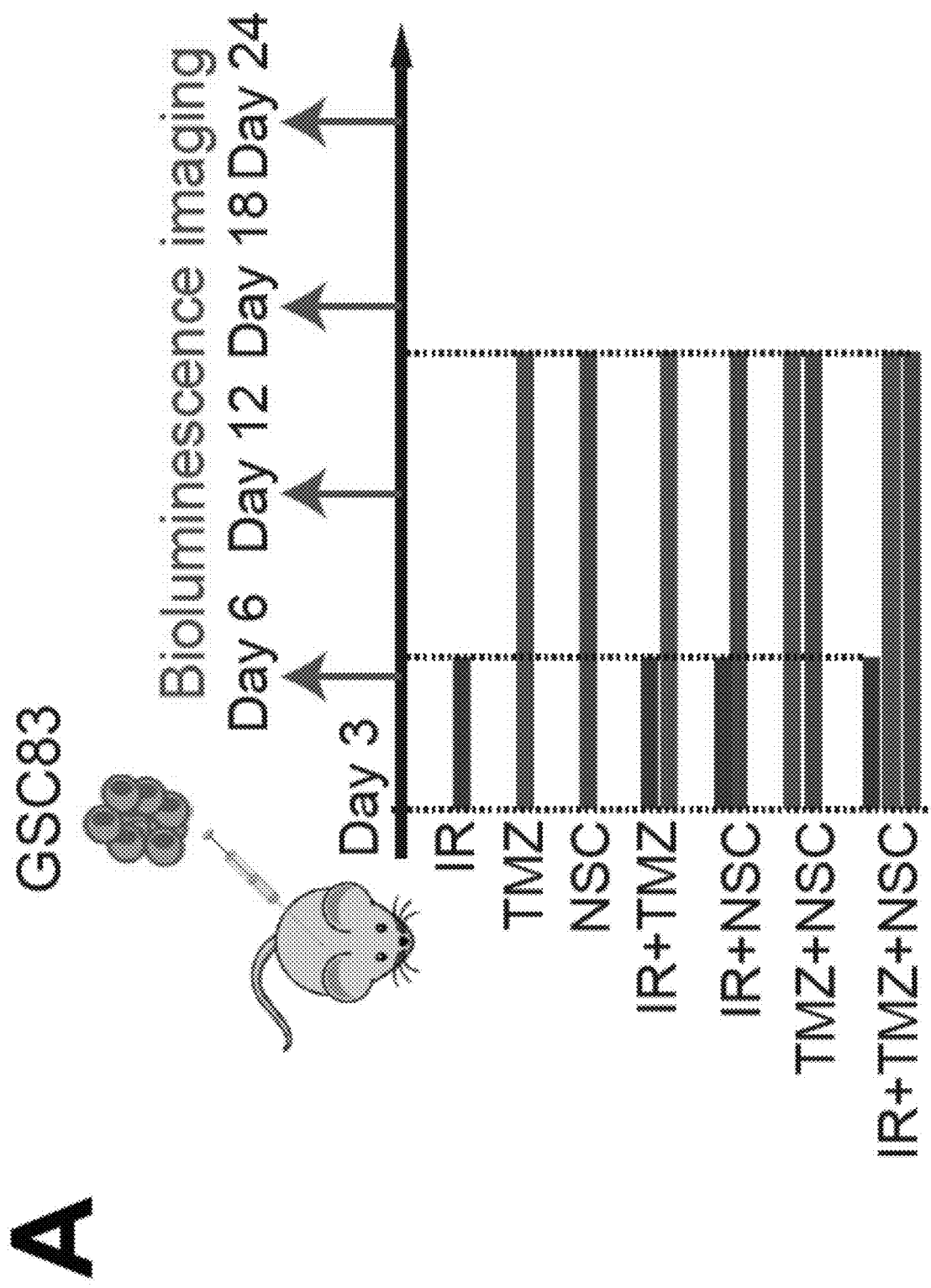
Figure 3:
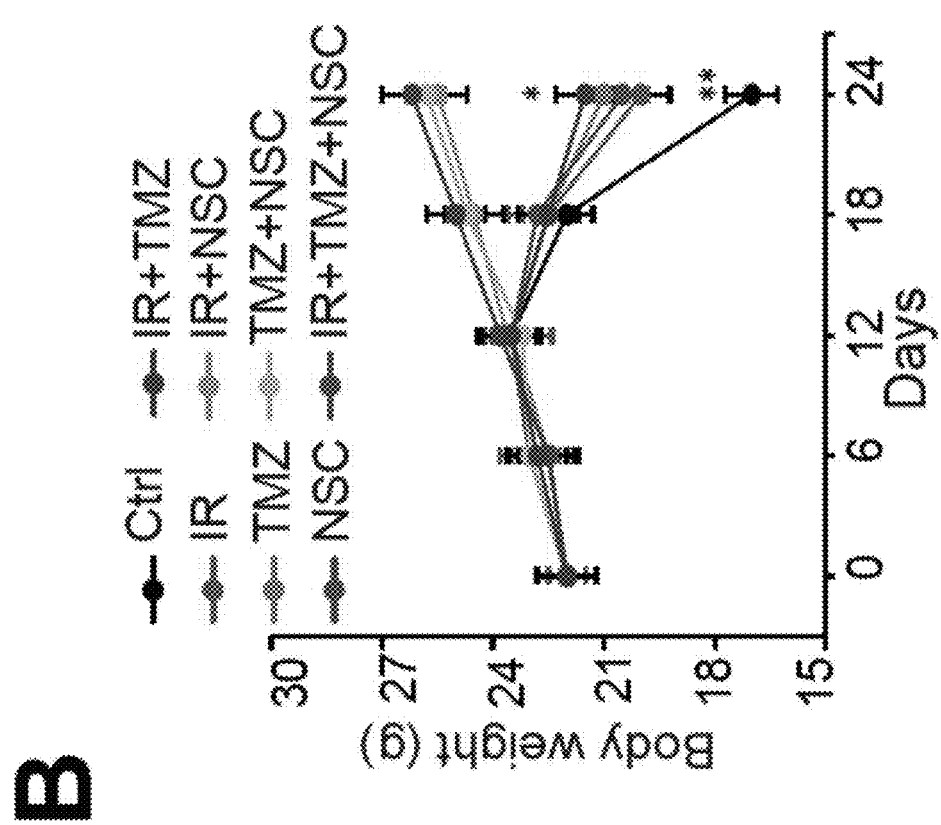
Figure 3:
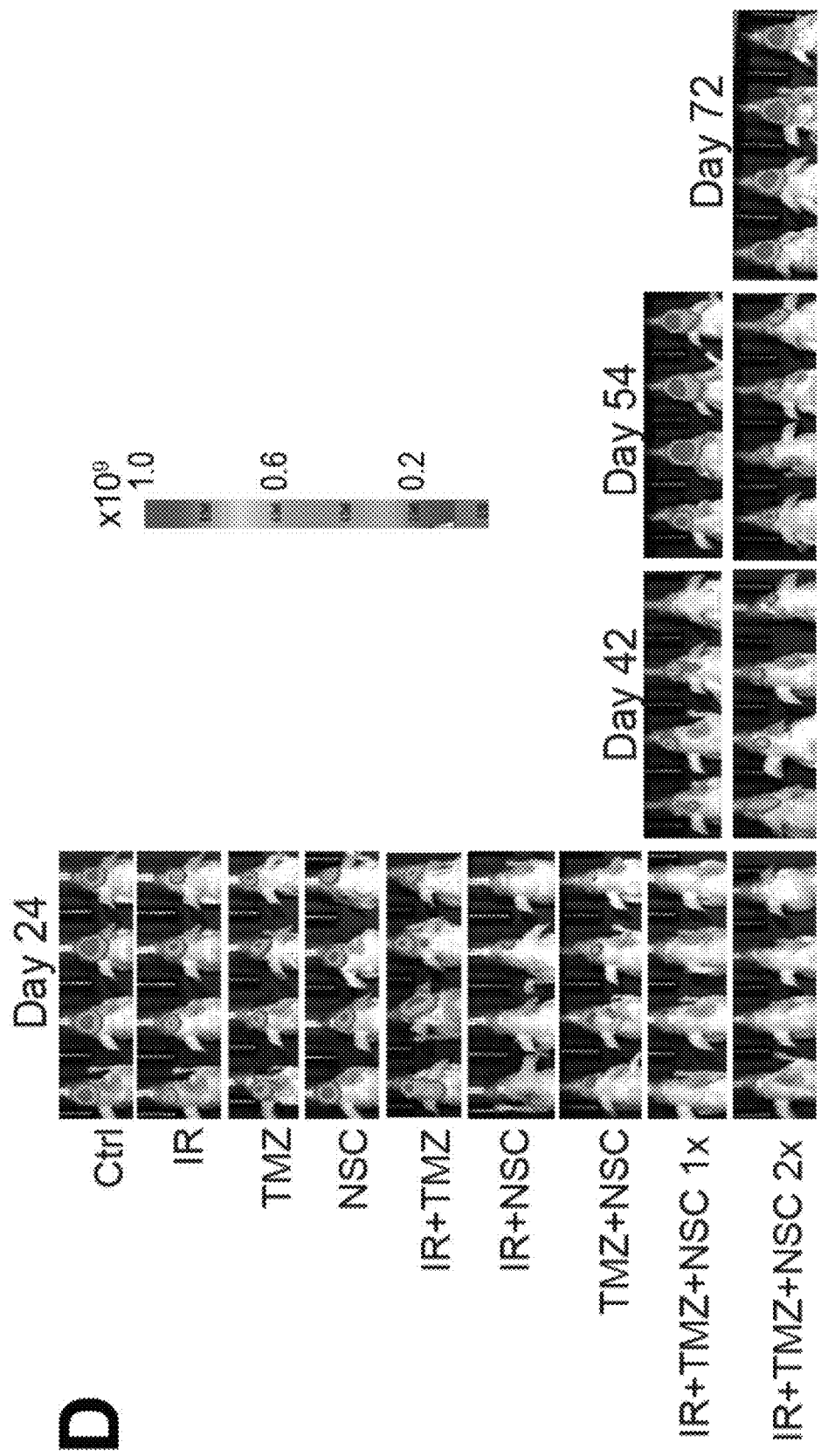
Figure 3:
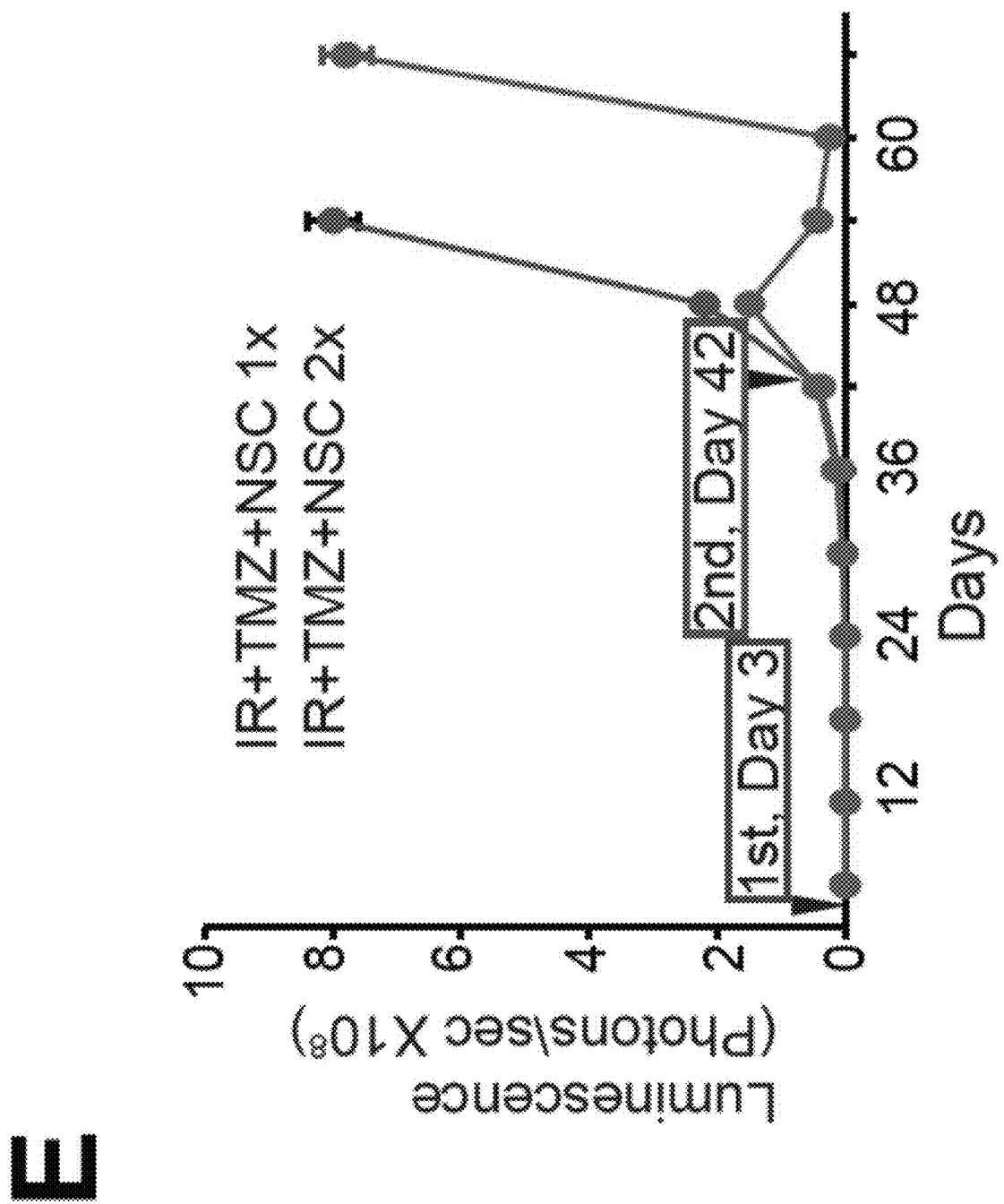
Figure 3:
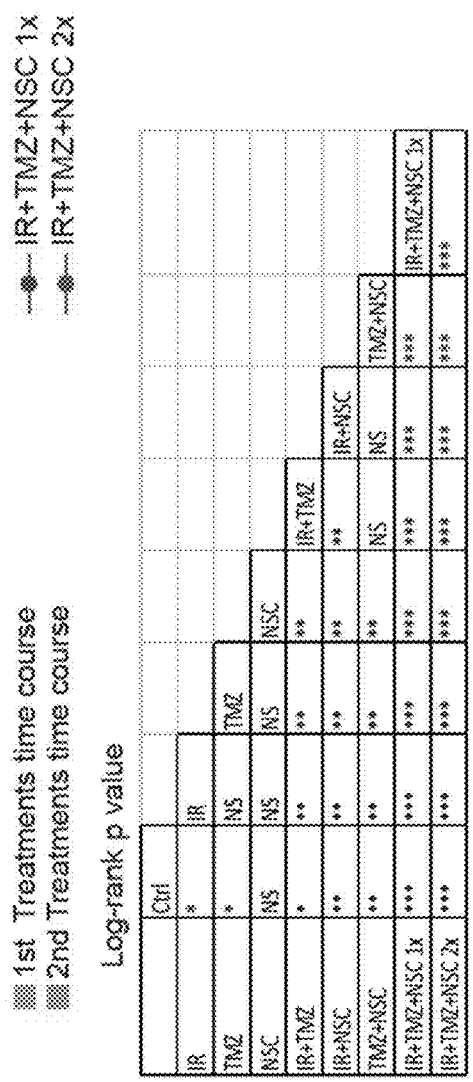
Figure 3:
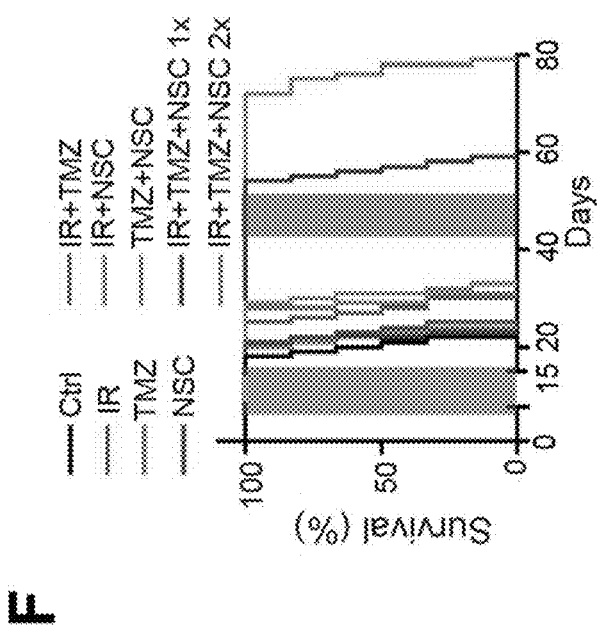

FIG. 3. Combination Therapy of Autophagy Inhibitor NSC185058 (NSC) with IR+TMZ Effectively Suppressed GSC83 Brain Tumor Xenograft Growth. (A) Designs for Combination Therapy of Targeting Autophagy using NSC (150 mg/kg, Monday, Wednesday, and Friday), IR (2 Gy/day for 5 consecutive days), TMZ (100 mg/kg/day), RT+NSC, TMZ+NSC or RT+TMZ+NSC for GSC83 orthotopic tumor xenograft model. (B) Changes in the body weight of the mice in each respective treatment groups. (C) Relative changes in the bioluminescence (BLI) of xenograft tumors formed by vehicle control and indicated treatment. Values represent the mean±SEM (n=8). *p<0.05, **p<0.01 compared to vehicle controls. (D) Effects of NSC, IR, TMZ and the indicated combinations on GSC83 brain tumor xenografts in mice. First and second IR+TMZ+NSC treatments were started at day 3 and day 42 post implantation, respectively. Mice were imaged at the indicated day after the implantation, and representative BLI images are shown. Colored scale bars represent photons/s/cm2/steradian. (E) The BLI of xenograft tumors formed by indicated treatment. (F) Kaplan-Meier (left) and log-rank p value analyses (right) of mice bearing GSC83 orthotopic xenografts with indicated treatments. Data are representative of two to three independent experiments with similar results. All bar plot data are means±SEM (n=8). *p<0.05, p<0.01, *p<0.001.

Figure 4:
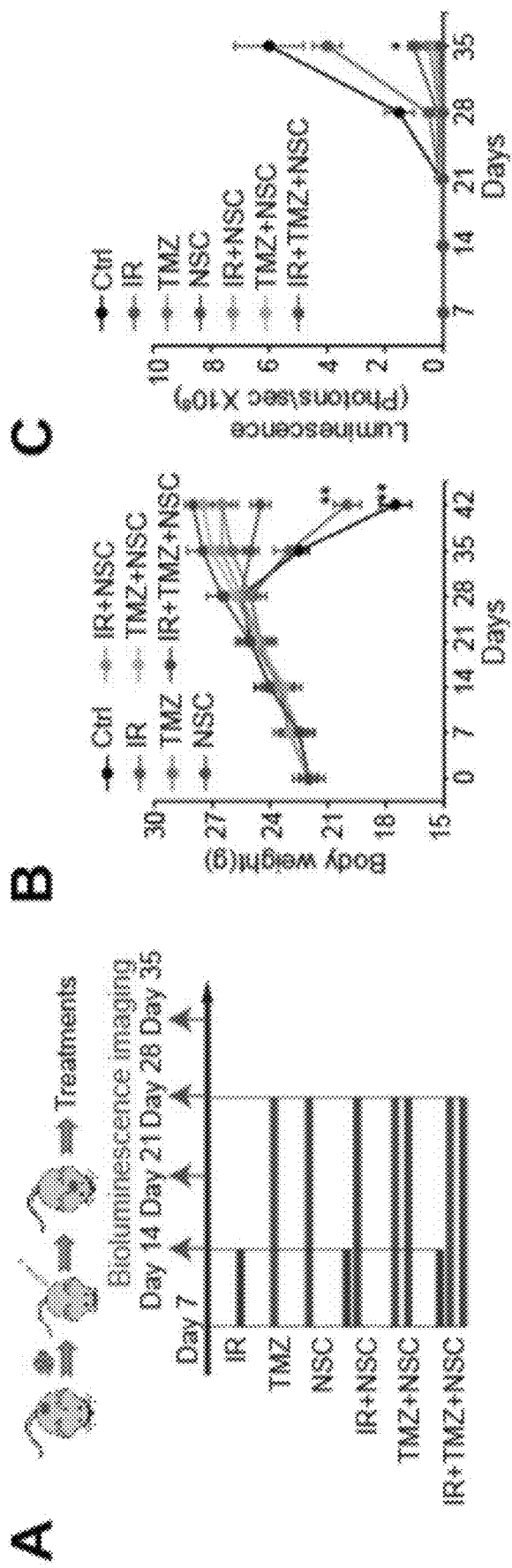
Figure 4:
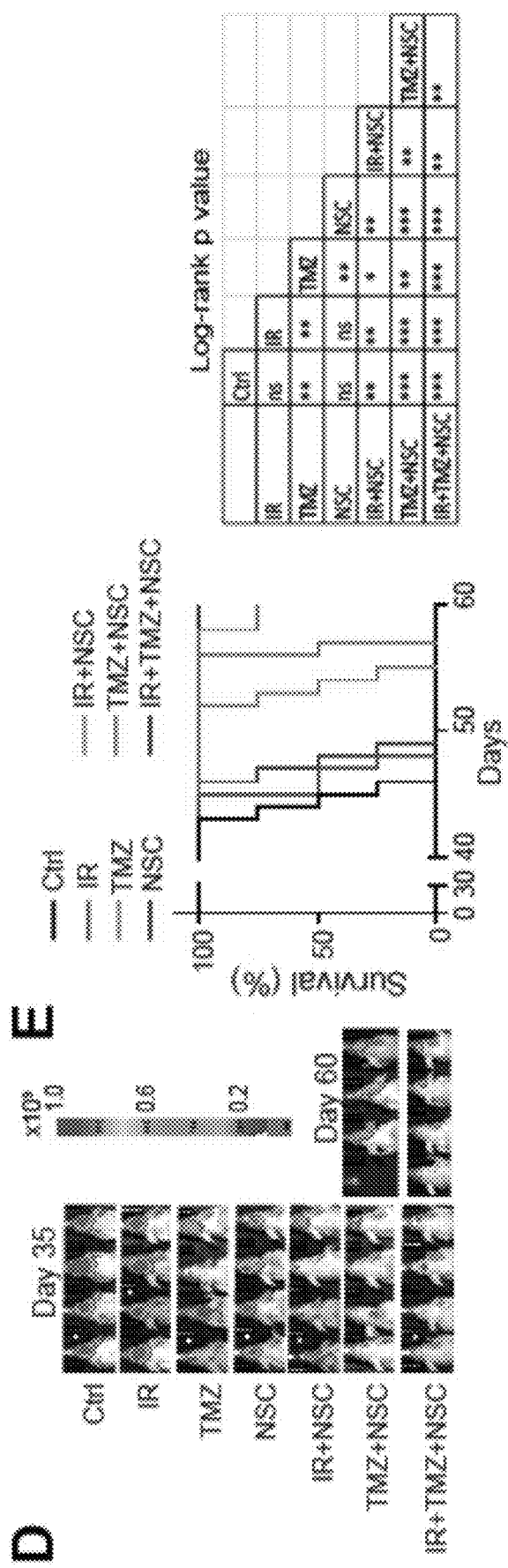

FIG. 4. Combination Therapy of Autophagy Inhibitor NSC185058 with TMZ or IR+TMZ Effectively Suppressed PDX GBM39 Brain Tumor Xenograft Growth. (A) Designs for Combination Therapy of Targeting Autophagy using NSC (150 mg/kg, Monday, Wednesday, and Friday), IR (2 Gy/day for 5 consecutive days), TMZ (100 mg/kg/day), RT+NSC, TMZ+NSC or RT+TMZ+NSC for PDX GBM39 model. (B) Body weight curves of different groups. Values represent the mean±SEM (n=8). *p<0.05, **p<0.01 compared to vehicle controls. (C) Relative changes in bioluminescent (BLI) signals of intracranial xenograft tumors with vehicle control or indicated treatment. n=8/group. *p<0.05, **p<0.01 compared to vehicle controls. Values represent the mean±SEM (n=8). *p<0.05, **p<0.01 compared to vehicle controls. (D) Representative bioluminescent images of mice-bearing intracranial xenografts with indicated treatments. NSC, IR, TMZ, and the indicated combinations. Treatments were started at day 7 post implantation. Mice were imaged after the last treatment. Colored scale bars represent photons/s/cm$^2$/steradian. (E) Kaplan-Meier (left) and log-rank p value analyses (right) of mice bearing GSC 83 orthotopic xenografts with indicated treatments. Data are representative of two to three independent experiments with similar results. All bar plot data are means±SEM. *p<0.05, p<0.01, *p<0.001.

Figure 5:
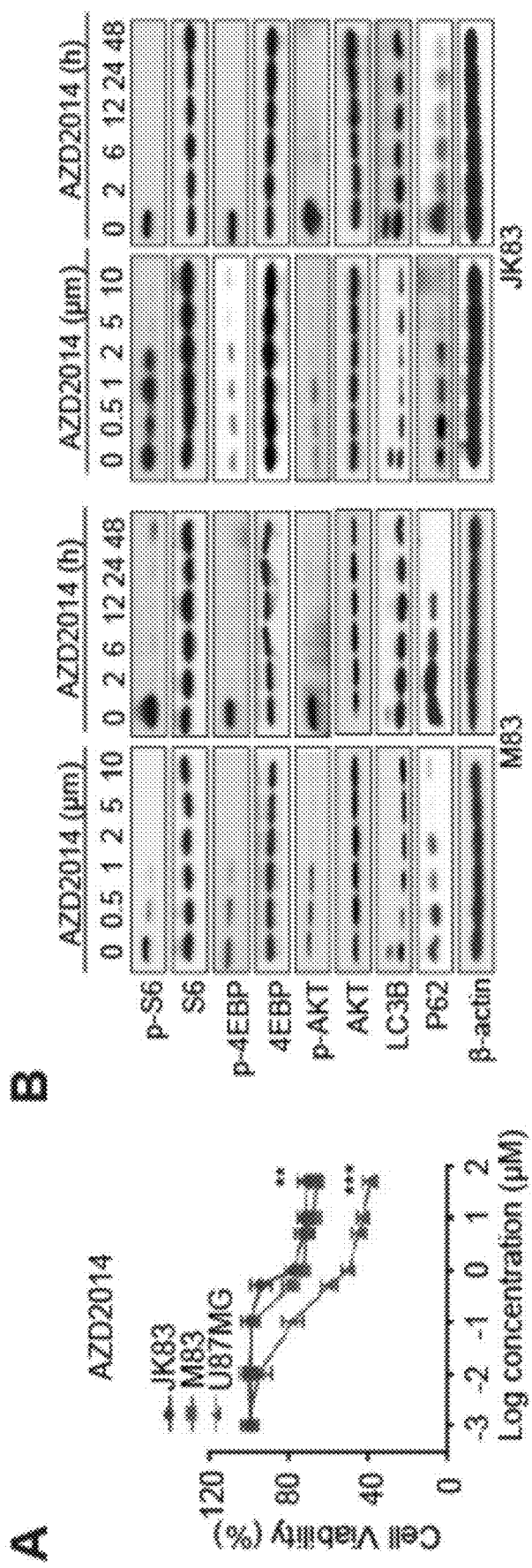

FIG. 5. A mTORC1/2 inhibitor AZD2014 inhibited cell survival, mTORC1 and mTORC2 activities in GSCs and glioma cells. (A) GSC M83 and JK83 and glioma cells U87 were treated with indicated concentration of AZD2014 for 72 h, then cell viability was evaluated. (B) GSC M83 and JK83 were treated with the indicated concentration of AZD2014 for 1 hr, or with 2 μM AZD2014 for the specified time. Cells were collected for immunoblot analysis. β-actin was used as a loading control; Results are representative of 2 independent experiments. *P<0.05, **P<0.01, paired two-way Student's t-test. Data are representative from three independent experiments with similar results.

Figure 6:
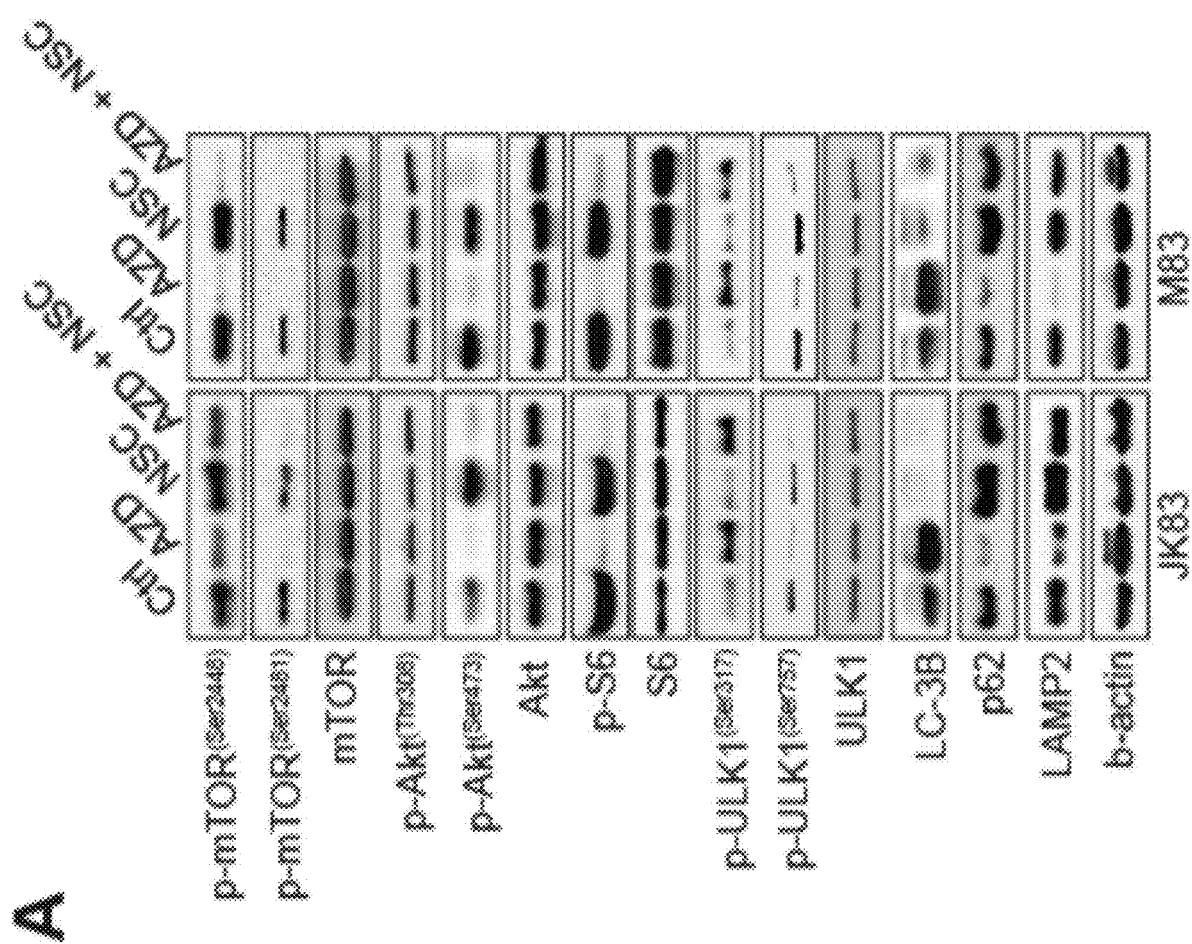
Figure 6:
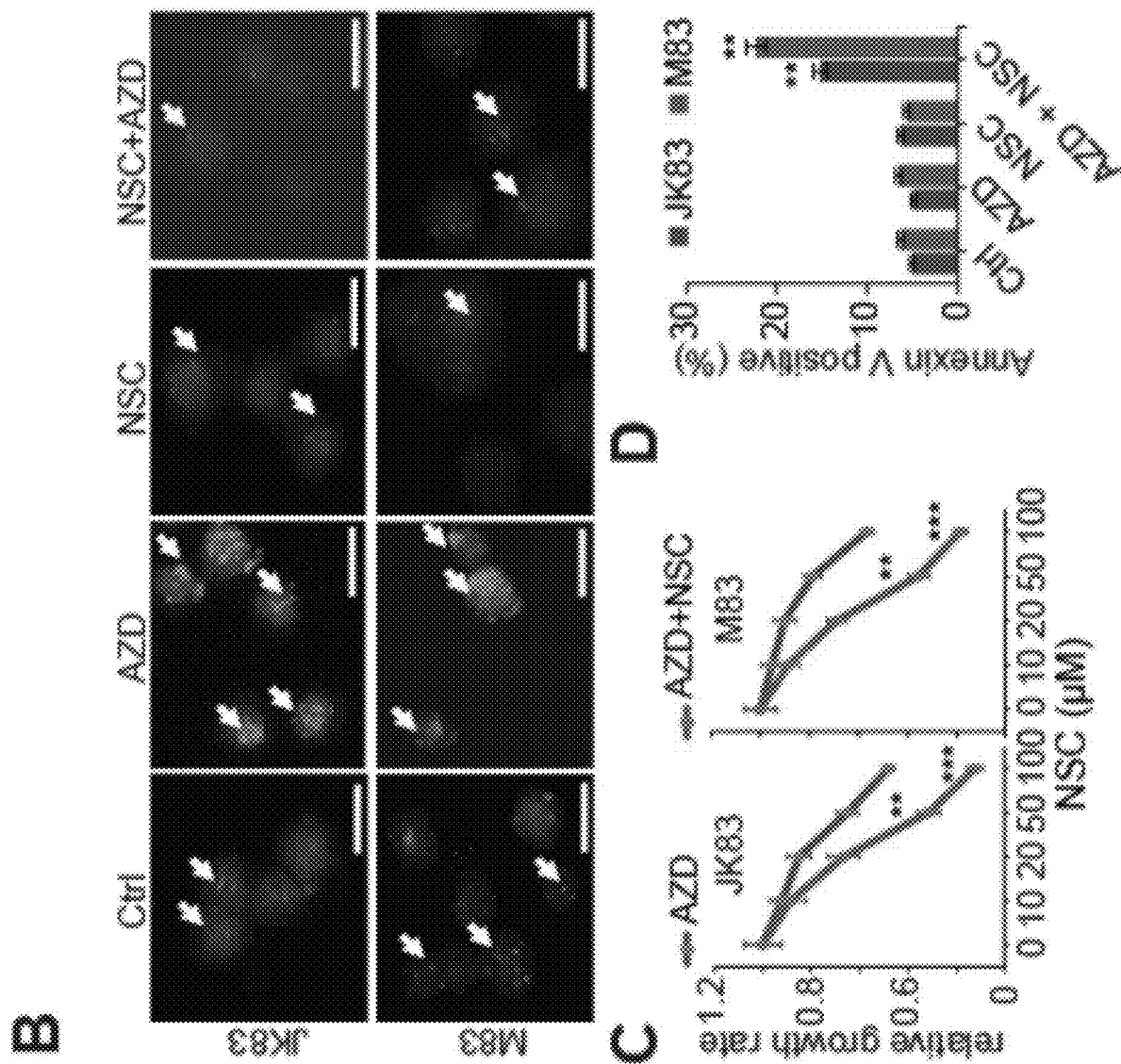

FIG. 6. NSC enhanced the cytotoxicity of a mTORC1/2 inhibitor AZD2014 in GSCs. (A) GSC M83 and JK83 were exposed to DMSO control vs AZD2014 vs NSCs vs AZD2014 in combination with NSC for 72 hr. Cells were collected for immunoblot analysis using indicated antibodies. (B) Immunofluorescence analyses for LC3B puncta in GSC M83 and JK83 cells with indicated treatments. (C and D) GSC M83 and JK83 and/or neural progenitor cells (NPC) were treated as indicated in (A), cell viability was tested at 72 h after treatment (C), and cell apoptosis was measured by Annexin V FACS assay 48 h after treatment. Data are representative from three independent experiments with similar results.

Figure 7:
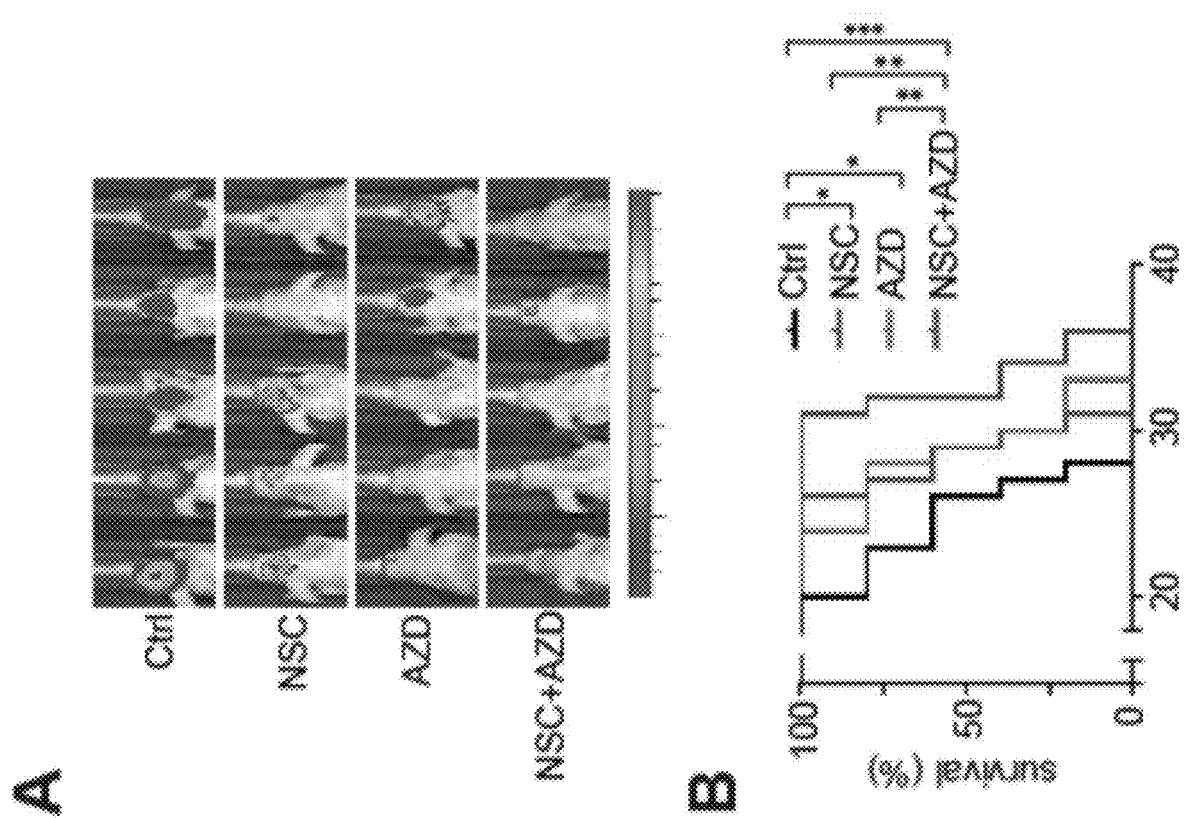
Figure 7:
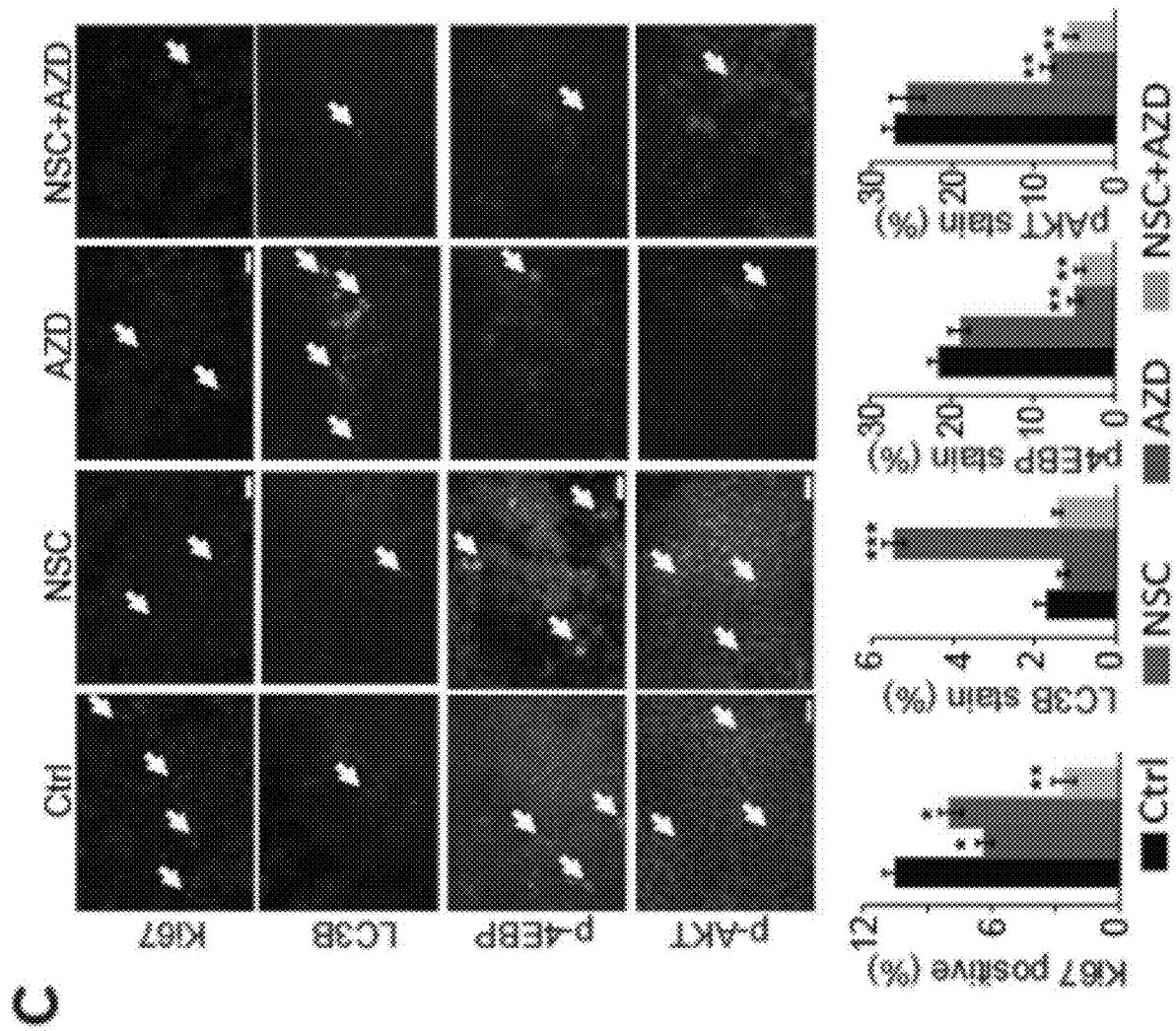

FIG. 7. NSC enhance anticancer efficacy of AZD2014 in a patient-derived GSC xenograft model. (A) Effects of NSC (150 mg/kg, M, W, F) and AZD2014 (50 mg/kg for 5 consecutive days) on GSC JK83 brain tumor xenografts in mice. Treatments were started at one week post-implantation. Bioluminescent (BLI) images were taken after the last treatment, and representative images are shown. Scale bar, photons/sec/cm2/steradian. (B) Kaplan-Meier of mice bearing GSC JK83 orthotopic xenografts with indicated treatments. (C) The brains of mice bearing orthotopic xenografts with indicated treatments were collected for immunohistochemical evaluation using indicating antibody. *P<0.05, p<0.01, *p<0.01. Data are representative from three independent experiments with similar results.

Figure 8:
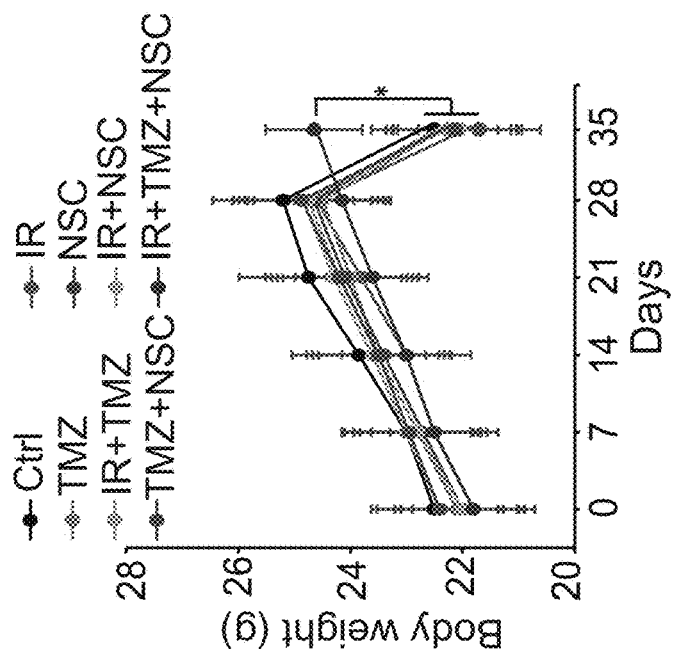
Figure 8:
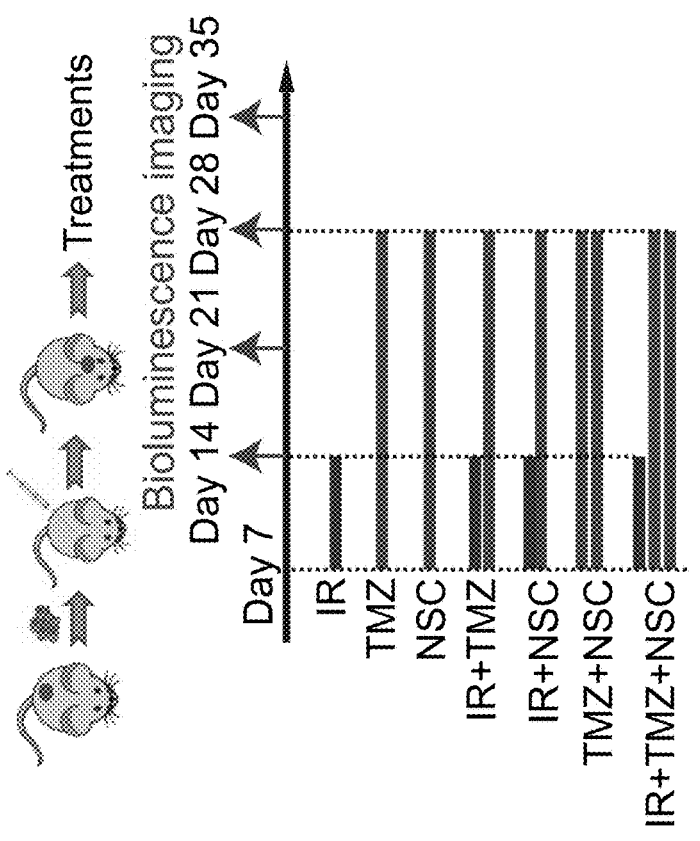
Figure 8:
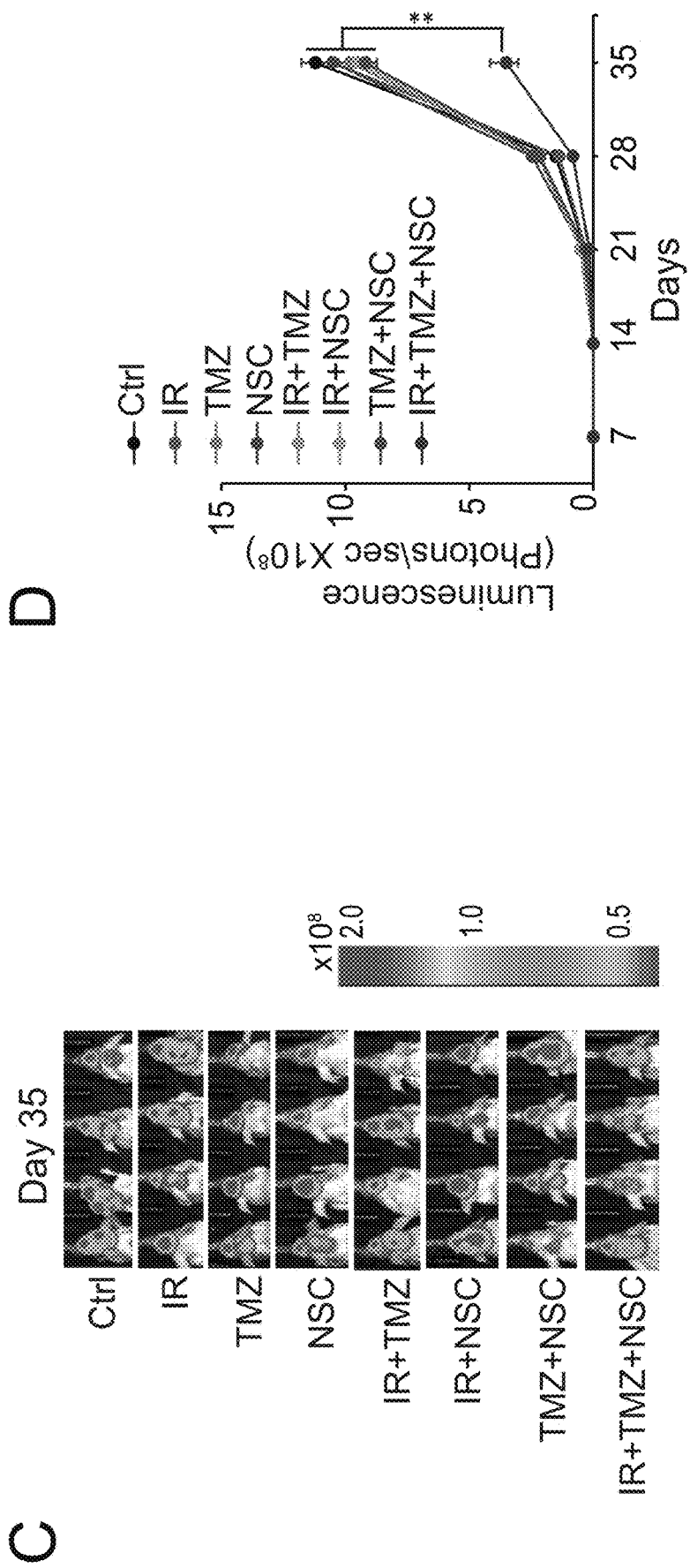
Figure 8:
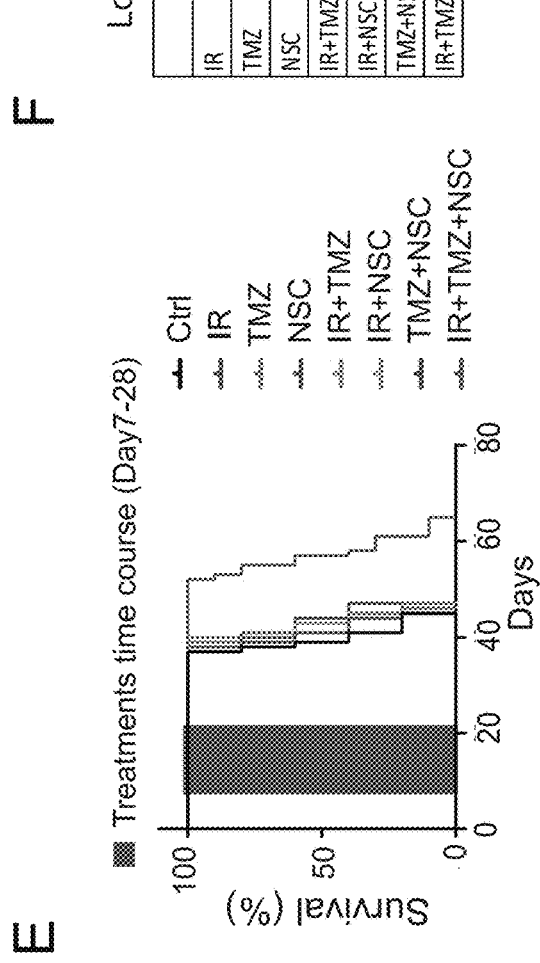

FIG. 8. Combination therapy of autophagy inhibitor NSC185058 (NSC) with IR+TMZ suppressed growth of intracranial GBM6FL temozolomide (TMZ) resistant (res) xenografts. (A) Designs for combination therapy of targeting autophagy using NSC (150 mg/kg, Monday, Wednesday, and Friday), IR (2 Gy/day for 5 consecutive days), TMZ (100 mg/kg/day), RT+NSC, TMZ+NSC or RT+TMZ+NSC for GBM6FL TMZ res orthotopic tumor xenograft model. Mice were imaged at the indicated day after the implantation, and representative BLI images are shown. (B) Changes in the body weight of the mice in each respective treatment groups. (C, D) Effects of NSC, IR, TMZ and the indicated combinations on GBM6FL TMZ res orthotopic xenografts in mice. The luminescence of xenograft tumors formed by indicated treatment. **p<0.01 compared to vehicle controls. Colored scale bars represent photons/s/cm2/steradian. (E, F) Kaplan-Meier (E) and log-rank p value analyses (F) of mice bearing GBM6FL TMZ res orthotopic xenografts with indicated treatments. First and second IR+TMZ+NSC tri-treatments were started at day 7 and day 35 post-implantation, respectively.

DETAILED DESCRIPTION

Disclosed are methods and compositions for treating, inhibiting, and/or preventing heterotopic ossification. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient.

As used herein, the term "subject" is meant to encompass a person who has a cell proliferative disease or disorder such as cancer. A "subject" may include a subject who has cancer of the brain, such as glioblastoma multiforme (GBM). A "subject" also may include a subject who has a cancer of the breast, lung, liver, head & neck, colon, prostate, pancreas, stomach, or other types of cancer.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "inhibit" means decreasing or blocking biological activity. For example, "inhibiting" may include reducing or blocking biological activity of the autophagy related 4B cysteine peptidase (ATG4B) protein.

The disclosed methods and compositions relate to treating cell proliferative diseases and disorders in a subject in need thereof. In some embodiments, the disclosed methods and compositions relate to treating a cell proliferative disease or disorder, such as glioblastoma multiforme (GBM), by administering a therapeutic agent that inhibits the biological activity of the autophagy related 4B cysteine peptidase (ATG4B) protein, and optionally, in conjunction, administering an additional therapeutic agent or a treatment that treats the cell proliferative disease or disorder.

The autophagy related 4B cysteine peptidase protein or "ATG4B," is cysteine protease required for the cytoplasm to vacuole transport (Cvt) and autophagy. (See Kabeya et al., "LC3, GABARAP and GATE16 localize to autophagosomal membrane depending on form-II formation," J. Cell. Sci. 117:2805-2812 (2004); and Tanida et al., "HsAtg4B/HsApg4B/autophagin-1 cleaves the carboxyl termini of three human Atg8 homologues and delipidates microtubule-associated protein light chain 3- and GABAA receptor-associated protein-phospholipid conjugates," J. Biol. Chem. 279:36268-36276 (2004); the contents of which are incorporated herein by reference in their entireties). ATG4B cleaves the C-terminal amino acid of ATG8 family proteins MAP1LC3, GABARAPL1, GABARAPL2, and GABARAP, to reveal a C-terminal glycine. Exposure of this C-terminal glycine is essential for ATG8 proteins conjugation to phosphatidylethanolamine (PE) and insertion to membranes, which is necessary for autophagy. ATG4B also functions as a delipidating enzyme for the PE-conjugated forms of MAP1LC3, GABARAPL1, GABARAPL2, and GABARAP. The ATG4B protein is assigned the Enzyme Commission (EC) number EC:3.4.22.-. The ATG4B protein alternatively may be referred to as cysteine protease ATG4B, AUT-like 1 cysteine endopeptidase, autophagin-1, autophagy-related cysteine endopeptidase 1, autophagy-related protein 4 homolog B, or hAPG4B.

There are several isoforms of human ATG4B having the following amino acid sequences SEQ ID NOs:1-5:

```
                                          SEQ ID NO: 1
MDAATLTYDT LRFAEFEDFP ETSEPVWILG RKYSIFTEKD

EILSDVASRL WFTYRKNFPA IGGTGPTSDT GWGCMLRCGQ

MIFAQALVCR HLGRDWRWTQ RKRQPDSYFS VLNAFIDRKD

SYYSIHQIAQ MGVGEGKSIG QWYGPNTVAQ VLKKLAVFDT

WSSLAVHIAM DNTVVMEEIR RLCRTSVPCA GATAFPADSD

RHCNGFPAGA EVTNRPSPWR PLVLLIPLRL GLTDINEAYV

ETLKHCFMMP QSLGVIGGKP NSAHYFIGYV GEELIYLDPH

TTQPAVEPTD GCFIPDESFH CQHPPCRMSI AELDPSIAVG

FFCKTEDDFN DWCQQVKKLS LLGGALPMFE LVELQPSHLA

CPDVLNLSLD SSDVERLERF FDSEDEDFEI LSL

SEQ ID NO: 2
MAHSVPSDSR GSVGGRTGKM DAATLTYDT LRFAEFEDFP

ETSEPVWILG RKYSIFTEKD EILSDVASRL

WFTYRKNFPA IGGTGPTSDT GWGCMLRCGQ MIFAQALVCR

HLGRDWRWTQ RKRQPDSYFS VLNAFIDRKD SYYSIHQIAQ

MGVGEGKSIG QWYGPNTVAQ VLKKLAVFDT WSSLAVHIAM

DNTVVMEEIR RLCRTSVPCA GATAFPADSD RHCNGFPAGA

EVTNRPSPWR PLVLLIPLRL GLTDINEAYV ETLKHCFMMP

QSLGVIGGKP NSAHYFIGYV GEELIYLDPH TTQPAVEPTD

GCFIPDESFH CQHPPCRMSI AELDPSIAVG FFCKTEDDFN

DWCQQVKKLS LLGGALPMFE LVELQPSHLA CPDVLNLSLG

ESCQVQILLM

SEQ ID NO: 3
MLRCGQ MIFAQALVCR HLGRDWRWTQ

RKRQPDSYFS VLNAFIDRKD SYYSIHQIAQ MGVGEGKSIG

QWYGPNTVAQ VLKKLAVFDT WSSLAVHIAM DNTVVMEEIR

RLCRTSVPCA GATAFPADSD RHCNGFPAGA EVTNRPSPWR

PLVLLIPLRL GLTDINEAYV ETLKHCFMMP QSLGVIGGKP

NSAHYFIGYV GEELIYLDPH TTQPAVEPTD GCFIPDESFH

CQHPPCRMSI AELDPSIAVG KQGRLVRSLI PWAPRPSSWC

AAVLGAAVVM CGTP

SEQ ID NO: 4
MLRCGQ MIFAQALVCR HLGRDWRWTQ

RKRQPDSYFS VLNAFIDRKD SYYSIHQIAQ MGVGEGKSIG
```

```
                        -continued
QWYGPNTVAQ  VLKKLAVFDT  WSSLAVHIAM  DNTVVMEEIR

RLCRTSVPCA  GATAFPADSD  RHCNGFPAGA  EVTNRPSPWR

PLVLLIPLRL  GLTDINEAYV  ETLKHCFMMP  QSLGVIGGKP

NSAHYFIGYV  GEELIYLDPH  TTQPAVEPTD  GCFIPDESFH

CQHPPCRMSI  AELDPSIAVG  FFCKTEDDFN  DWCQQVKKLS

LLGGALPMFE  LVELQPSH L  GESCQVQVGS  LG A

CPDVLNLSLD  SSDVERLERF  FDSEDEDFEI  LSL

SEQ ID NO: 5
MDAATLTYDT  LRFAEFEDFP  ETSEPVWILG  RKYSIFTEKD

EILSDVASRL  WFTYRKNFPA  IGGTGPTSDT  GWGCMLRCGQ

MIFAQALVCR  HLGRDWRWTQ  RKRQPDSYFS  VLNAFIDRKD

SYYSIHQIAQ  MGVGEGKSIG  QWYGPNTVAQ  VLKKLAVFDT

WSSLAVHIAM  DNTVVMEEIR  RLCRTSVPCA  GATAFPADSD

RHCNGFPAGA  EVTNRPSPWR  PLVLLIPLRL  GLTDINEAYV

ETLKHCFMMP  QSLGVIGGKP  NSAHYFIGYV  GEELIYLDPH

TTQPAVEPTD  GCFIPDESFH  CQHPPCRMSI  AELDPSIAVG

FFCKTEDDFN  DWCQQVKKLS  LLGGALPMFE  LVELQPSHLA

CPDVLNLSL   GESCQVQILL  M
```

As such, the disclosed methods may utilize and/or the disclosed compositions may comprise one or more therapeutic agents that inhibit one or more biological activities of ATG4B, which may include, but are not limited to cysteine catalyzed peptidase activity (e.g., cleavage the carboxyl termini of three human Atg8 homologues) and/or delipidase activity (e.g., delipidation of microtubule-associated protein light chain 3- and GABAA receptor-associated protein-phospholipid conjugates). Agents that inhibit the biological activity of ATG4B are known in the art. (See Akin et al., "A novel ATG4B antagonist inhibits autophage and has a negative impact on osteosarcoma tumors," Autophagy 10:11, 2021-2035; November 2014; and Bosc et al., "A new quinolone-based chemical probe inhibits the autophagy-related cysteine protease ATG4B, Scientific Reports (2018) 8:11653, 1-17; the contents of which are incorporated herein by reference in their entireties).

Agents that inhibit the biological activity of ATG4B may include, but are not limited to the compound referred to as NSC 185058, CAS 39122-38-8, N-pyridin-2-yl-pyridine-2-carbothioamide, having the following formula or a salt thereof:

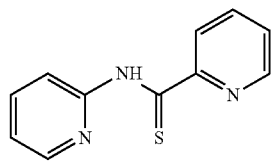 [SMILES: S=C(Nc1ccccn1)c1ccccn1]

Agents that inhibit the biological activity of ATG4B may include, but are not limited to the compound referred to as NSC 377071, CAS 26097-80-3, Novazole, Cambendazole, Propan-2-yl N-[2-(1,3-thiazol-4-yl)-3H-benzimidazol-5-yl] carbamate, having the following formula or a salt thereof:

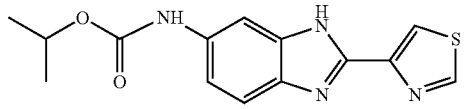 [SMILES: CC(C)OC(=O)Nc1ccc2nc(-c3cscn3)[nH]c2c1]

Agents that inhibit the biological activity of ATG4B may include, but are not limited to the compound having the following formula or a salt thereof:

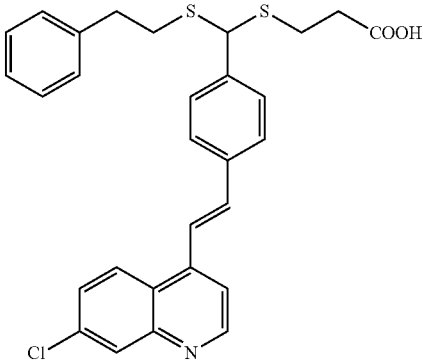 [SMILES: O=C(O)CCSC(SCCc1ccccc1)c1ccc(/C=C/c2ccnc3cc(Cl)ccc23)cc1]

In some embodiments, the disclosed methods and compositions relate to treating a cell proliferative disease or disorder in in a subject in need thereof by administering to the subject a therapeutic agent that comprises an alkylating agent. For example, in some embodiments, the disclosed methods and composition relate to treating a cell proliferative disease or disorder by administering to a subject in need thereof a therapeutic agent that inhibits the biological activity of ATG4B and administering to the subject an alkylating agent. The alkylating agent may be administered to the subject before, concurrently with, or after the therapeutic agent that inhibits the biological activity of ATG4B is administered to the subject. Suitable alkylating agents for the disclosed methods and compositions may include, but are not limited to, triazines (e.g., temozolomide, and decarbazine), ethylenimines (e.g., altretamine, and thiotepa), alky sulfonates (e.g., busulfan), nitrosoureas (e.g., carmustine, lomustine, and steptozocin), nitrogen mustards (e.g., bendamustine, chlorambucil, cyclophosphamide, ifosfamide, mechlorethamine, and melphalan), isoquinolines or tetrahydroisoquinolines (e.g., trabectedin), and carbolines or tetrahydro-β-carbolines (e.g., luribectedin).

In some embodiments, the disclosed methods and compositions relate to treating a cell proliferative disease or disorder in in a subject in need thereof by administering to the subject a therapeutic agent that inhibits the biological activity of the mammalian target of rapamycin (mTOR). (See Xie et al., "mTOR inhibitors in cancer therapy," F1000 Research, 2016, 5(F1000 Faculty Rev):20178; the content of which is incorporated herein by reference in its entirety). As known in the art, mTOR is a serine/threonine protein kinase which regulates cellular metabolism, grown, and survival in response to growth factors, hormones, and stress signals. In some embodiments, the disclosed methods and composition relate to treating a cell proliferative disease or disorder by administering to a subject in need thereof a therapeutic agent that inhibits the biological activity of ATG4B and administering to the subject a therapeutic agent that inhibits the biological activity of mTOR (e.g., an inhibitor of the kinase activity of mTOR). The therapeutic agent that inhibits the biological activity of mTOR may be administered to the subject before, concurrently with, or after the therapeutic agent that inhibits the biological activity of ATG4B is administered to the subject.

Suitable agents that inhibit the biological activity of mTOR may include, but are not limited to the compound referred to as vistusertib (AZD2014) having the following formula or salt thereof:

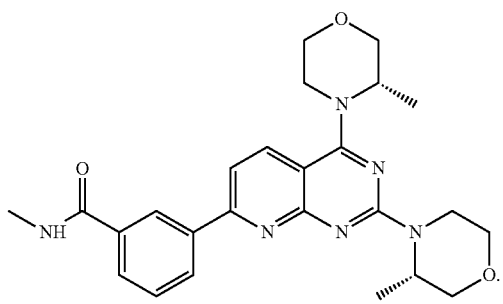 [SMILES: CNC(=O)c1cccc(-c2ccc3c(N4CCOC[C@@H]4C)nc(N4CCOC[C@@H]4C)nc3n2)c1]

Suitable agents that inhibit the biological activity of mTOR may include, but are not limited to the compound referred to as vistusertib (AZD8055) having the following formula or salt thereof:

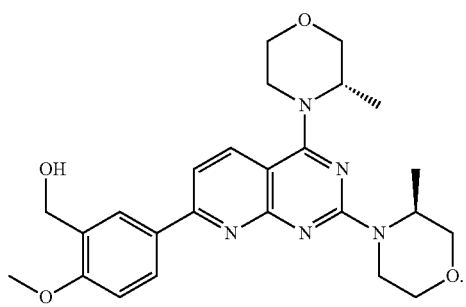

Suitable agents that inhibit the biological activity of mTOR may include, but are not limited to the compound referred to as sapanisertib (TAK-288 or INK128 formerly MLN0128) having the following formula or salt thereof:

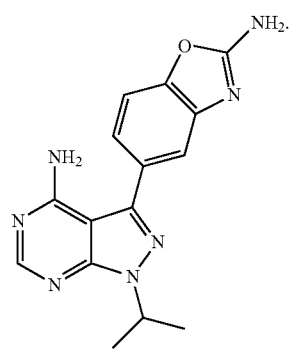 [SMILES: CC(C)n1nc(-c2ccc3oc(N)nc3c2)c2c(N)ncnc21]

Suitable agents that inhibit the biological activity of mTOR may include, but are not limited to the compound referred to as dactolisib (NVP-BEZ235 and BEZ-235) having the following formula or salt thereof:

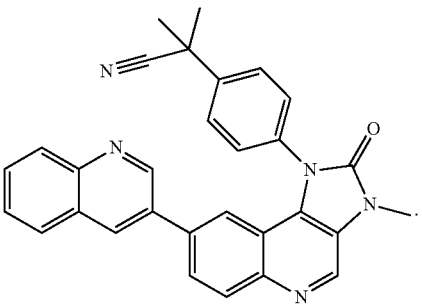 [SMILES: Cn1c(=O)n(-c2ccc(C(C)(C)C#N)cc2)c2c3cc(-c4cnc5ccccc5c4)ccc3ncc21]

Suitable agents that inhibit the biological activity of mTOR may include, but are not limited to the compound referred to as OSI027 having the following formula or salt thereof:

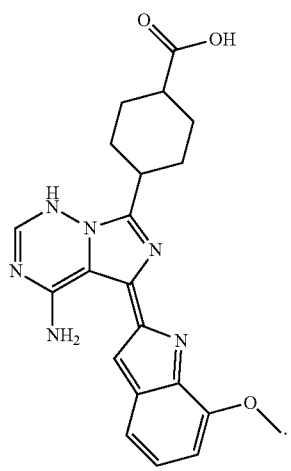 [SMILES: COc1cccc2c1=N/C(=c1\nc(C3CCC(C(=O)O)CC3)n3c1=C(N)N=CN3)C=2]

Suitable agents that inhibit the biological activity of mTOR may include, but are not limited to the compound referred to as XL765 having the following formula or salt thereof:

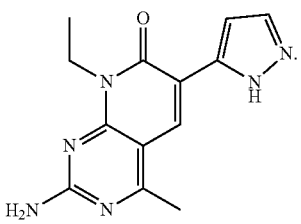

Other suitable therapeutic agents that inhibits the biological activity of mTOR for the disclosed methods and compositions may include, but are not limited to sirolimus, temsirolimus, everolimus, and ridaforolimus.

In some embodiments, the disclosed methods and compositions relate to treating a cell proliferative disease or disorder in in a subject in need thereof by administering to the subject radiation therapy. ATG4B activity has been shown to regulate radioresistance in glioblastoma. (See Huang et al., MST4 Phosphorylation of ATG4B Regulates Autophagic Activity, Tumorigenicity, and Radioresistance in Glioblasoma," Cancer Cell (2017), 32, 840-855, the content of which is incorporated herein by reference in its entirety). In some embodiments, the disclosed methods and composition relate to treating a cell proliferative disease or disorder by administering to a subject in need thereof a therapeutic agent that inhibits the biological activity of ATG4B and administering to the subject radiation therapy. The radiation therapy may be administered to the subject before, concurrently with, or after the therapeutic agent that inhibits the biological activity of ATG4B is administered to the subject.

In some embodiments, the disclosed methods and compositions relate to treating a cell proliferative disease or disorder in in a subject in need thereof by administering to the subject a combination of therapies selected from (i) administering a therapeutic agent that inhibits the biological activity of ATG4B to the subject; and/or (ii) administering an alkylating agent to the subject (e.g., temozolomide); and/or (iii) administering a therapeutic agent that inhibits the biological activity of ATG4B to the subject; and/or (iv) administering radiation therapy to the subject. Suitable subject may include, but are not limited to subjects having brain cancer such as glioblastoma multiforme (GBM). The combined treatment of administering radiation therapy and temozolomide is referred to as the "Stupp Protocol." In some embodiments, of the disclosed methods, a subject undergoing the Stupp Protocol is administered a therapeutic agent that inhibits the biological activity of ATG4B, either before, concurrently with, or after the Stupp Protocol.

In the disclosed methods, the therapeutic agents may be administered by any suitable route of administration. In some embodiments, the therapeutic agents of the disclosed methods and compositions may be administered by any suitable route of delivery, including but not limited to, oral delivery and intravenous delivery.

ILLUSTRATIVE EMBODIMENTS

The following Embodiments are illustrative and should not be interpreted to limit the scope of the claimed subject matter.

Embodiment 1

A method for treating a cell proliferative disease or disorder in a subject in need thereof, the method comprising (i) administering to the subject a therapeutic agent that inhibits the biological activity of ATG4B; (ii) administering to the subject an alkylating agent; and (iii) administering to the subject radiotherapy.

Embodiment 2

The method of embodiment 1, wherein the cell proliferative disease or disorder is cancer.

Embodiment 3

The method of embodiment 2, wherein the cancer is glioblastoma.

Embodiment 4

The method of embodiment 2, wherein the cancer is selected from cancer of the breast, the lung, the liver, the head & the neck, the colon, the prostate, the pancreas, and the stomach.

Embodiment 5

The method of any of the foregoing embodiments, wherein the therapeutic agent that inhibits the biological activity of ATG4B comprises a compound referred to as NSC 185058, CAS 39122-38-8, N-pyridin-2-yl-pyridine-2-carbothioamide, having the following formula or a salt thereof:

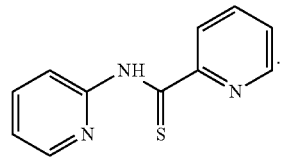 [SMILES: S=C(Nc1ccccn1)c1ccccn1]

Embodiment 6

The method of any of the foregoing embodiments, wherein the therapeutic agent that inhibits the biological activity of ATG4B comprises a compound referred to as NSC 377071, CAS 26097-80-3, Novazole, Cambendazole, Propan-2-yl N-[2-(1,3-thiazol-4-yl)-3H-benzimidazol-5-yl]carbamate, having the following formula or a salt thereof:

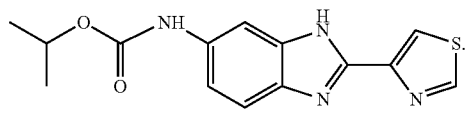

Embodiment 7

The method of any of the foregoing embodiments, wherein the therapeutic agent that inhibits the biological activity of ATG4B comprises a compound having the following formula or a salt thereof:

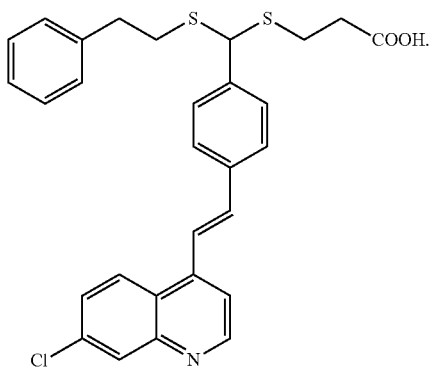 [SMILES: O=C(O)CCSC(SCCc1ccccc1)c1ccc(/C=C/c2ccnc3cc(Cl)ccc23)cc1]

Embodiment 8

The method of any of the foregoing embodiments, wherein the alkylating agent is selected from triazines (e.g., temozolomide, and decarbazine), ethylenimines (e.g., altretamine, and thiotepa), alky sulfonates (e.g., busulfan), nitrosoureas (e.g., carmustine, lomustine, and steptozocin), and nitrogen mustards (e.g., bendamustine, chlorambucil, cyclophosphamide, ifosfamide, mechlorethamine, and melphalan).

Embodiment 9

A method for treating a cell proliferative disease or disorder in a subject in need thereof, the method comprising (i) administering to the subject a therapeutic agent that inhibits the biological activity of ATG4B; and (ii) administering to the subject a therapeutic agents that inhibits the biological activity of mTOR.

Embodiment 10

The method of embodiment 9 further comprising (iii) administering to the subject an alkylating agent such as temozolimide (TMZ).

Embodiment 11

The method of embodiment 9 or 10 further comprising (iv) administering to the subject radiotherapy.

Embodiment 12

The method of any of embodiments 9-11, wherein the cell proliferative disease or disorder is cancer.

Embodiment 13

The method of embodiment 12, wherein the cancer is glioblastoma.

Embodiment 14

The method of embodiment 12, wherein the cancer is selected from cancer of the breast, the lung, the liver, the head & the neck, the colon, the prostate, the pancreas, and the stomach.

Embodiment 15

The method of any of embodiments 9-14, wherein the therapeutic agent that inhibits the biological activity of ATG4B comprises a compound referred to as NSC 185058, CAS 39122-38-8, N-pyridin-2-yl-pyridine-2-carbothioamide, having the following formula or a salt thereof:

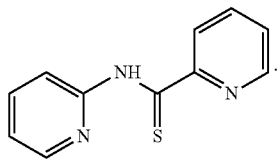

Embodiment 16

The method of any of embodiments 9-14, wherein the therapeutic agent that inhibits the biological activity of ATG4B comprises a compound referred to as NSC 377071, CAS 26097-80-3, Novazole, Cambendazole, Propan-2-yl N-[2-(1,3-thiazol-4-yl)-3H-benzimidazol-5-yl]carbamate, having the following formula or a salt thereof:

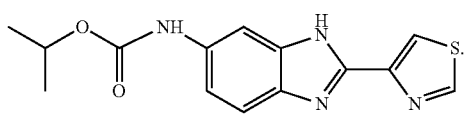 [SMILES: CC(C)OC(=O)Nc1ccc2nc(-c3cscn3)[nH]c2c1]

Embodiment 17

The method of any of embodiments 9-14, wherein the therapeutic agent that inhibits the biological activity of ATG4B comprises a compound having the following formula or a salt thereof:

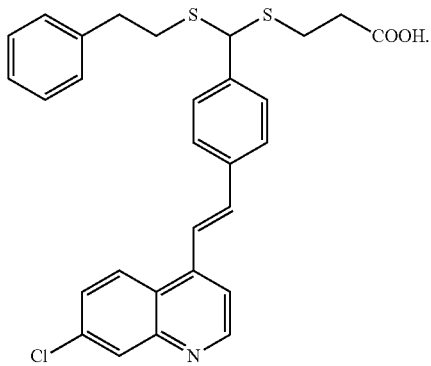 [SMILES: O=C(O)CCSC(SCCc1ccccc1)c1ccc(/C=C/c2ccnc3cc(Cl)ccc23)cc1]

Embodiment 18

The method of any of embodiments 9-17, wherein the therapeutic agent that inhibits the biological activity of mTOR comprises the compound referred to as vistusertib (AZD2014) having the following formula or salt thereof:

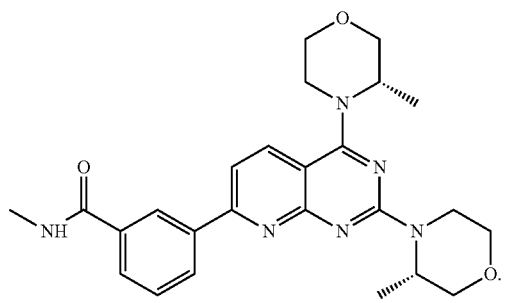 [SMILES: CNC(=O)c1cccc(-c2ccc3c(N4CCOC[C@@H]4C)nc(N4CCOC[C@@H]4C)nc3n2)c1]

Embodiment 19

The method of any of embodiments 9-17, wherein the therapeutic agent that inhibits the biological activity of mTOR comprises the compound referred to as AZD8055 having the following formula or salt thereof:

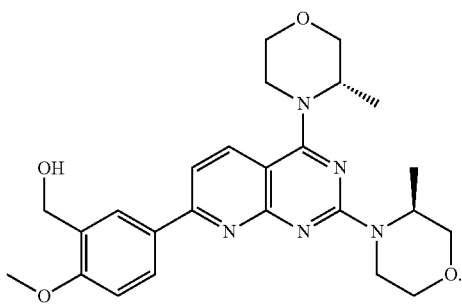

Embodiment 20

The method of any of embodiments 9-17, wherein the therapeutic agent that inhibits the biological activity of mTOR comprises the compound referred to as sapanisertib (TAK-288 or INK128 formerly MLN0128) having the following formula or salt thereof:

Embodiment 21

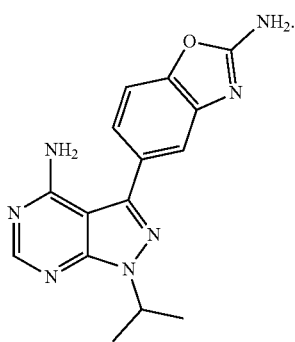 [SMILES: CC(C)n1nc(-c2ccc3oc(N)nc3c2)c2c(N)ncnc21]

The method of any of embodiments 9-17, wherein the therapeutic agent that inhibits the biological activity of mTOR comprises the compound referred to as dactolisib (NVP-BEZ235 and BEZ-235) having the following formula or salt thereof:

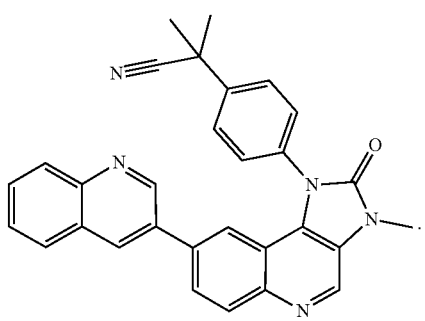 [SMILES: Cn1c(=O)n(-c2ccc(C(C)(C)C#N)cc2)c2c3cc(-c4cnc5ccccc5c4)ccc3ncc21]

Embodiment 22

The method of any of embodiments 9-17, wherein the therapeutic agent that inhibits the biological activity of mTOR comprises the compound referred to as OSI027 having the following formula or salt thereof:

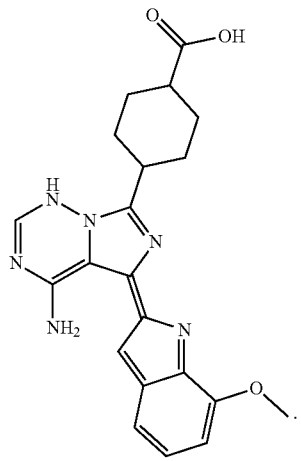 [SMILES: COc1cccc2c1=N/C(=c1\nc(C3CCC(C(=O)O)CC3)n3c1=C(N)N=CN3)C=2]

Embodiment 23

The method of any of embodiments 9-17, wherein the therapeutic agent that inhibits the biological activity of mTOR comprises the compound referred to as XL765 having the following formula or salt thereof:

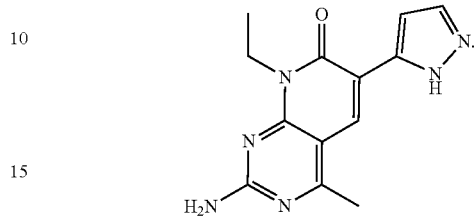

Embodiment 24

The method of any of embodiments 9-17, wherein the therapeutic agent that inhibits the biological activity of mTOR comprises the compound referred to as sirolimus, temsirolimus, everolimus, or ridaforolimus.

EXAMPLES

The following Examples are illustrative and should not be interpreted to limit the scope of the claimed subject matter.

Title: Methods for Enhancing Anti-Glioma Effects of Cytotoxic Therapies Through Inhibiting ATG4B/Autophagy Activities Abstract The present inventors disclose novel methods to enhance the activity of convention genotoxic therapy (radiotherapy, RT, and temozolomide, TMZ), as well as targeted small molecule inhibitor therapy (mTOR therapy), through use of a novel autophagy/ATG4B inhibitor NSC185058 when treating glioblastoma (GBM). Furthermore, NSC185058 was delivered to a glioma tumor xenograft in the brain of animals at sufficient levels to inhibit autophagy, and did not display any toxic effects on the animals.

Applications

Applications of the disclosed technology may include, but are not limited to: (i) Inhibiting ATG4B-dependent autophagy with NSC185058 and reducing or inhibiting the cytoprotective autophagic response of cancer cells and/or increasing the effectiveness of first-line standard therapies (e.g. radiation therapy (RT) and temozolomide (TMZ)) for treating glioblastoma (GBM); (ii) Inhibiting ATG4B-dependent autophagy with NSC185058 and reducing or inhibiting the cytoprotective autophagic response of cancer cells and increasing the effectiveness of small molecule targeted therapies (e.g., mTOR inhibitor therapy) for treating glioblastoma; (iii) Inhibiting ATG4B-dependent autophagy with NSC185058 and reducing or inhibiting the cytoprotective autophagic response of cancer cells and/or increasing the effectiveness of first-line standard therapies, including, but not limited to cancers of the brain (e.g., glioblastoma, GBM), breast, lung, liver, and head & neck cancers.

Advantages

Advantages of the disclosed technology may include, but are not limited to: (i) NSC185058 exhibited no relevant tissue toxicity in treated mice and excellent blood/brain barrier (BBB) penetration; (ii) NSC185058 was maintained at concentration levels that were effective on inhibiting brain tumors in brain and plasma; (iii) compared to other known autophagy inhibitors such as chloroquine (CQ) and hydroxy-CQ (HCQ), ATG4B inhibitor NSC185058 displays highly specific activities against autophagy and provides better inhibitory effects in combination treatments with RT, TMZ, and small molecule inhibitors of mTOR.

Background

Autophagy is an essential cellular process for the catabolism of proteins and damaged organelles in a lysosome-dependent manner (Levine and Kroemer, 2008). Cancer cells employed autophagy to remove damaged organelles and aggregated proteins, and to recycle nutrients in high demand to support tumor growth (Amaravadi et al., 2016). Radiation Therapy (RT) and Temozolomide (TMZ) are front-line treatments for many types of cancers including GBM, but trigger the autophagic response in tumor cells, which contributes to tumor's acquisition of resistance to treatment (Janku et al., 2011).

Due to deletions or mutations of PTEN, the phosphatidylinositol 3-kinase (PI3K)/Akt/mammalian target of rapamycin (mTOR) pathways are over-activated in near 30% of GBMs, resulting in tumorigenicity and progression (Van Meir et al., 2010). mTOR is a serine/threonine protein kinase that exists in two distinct complexes: mTOR complex 1 (mTORC1) and mTOR complex 2 (Saxton and Sabatini, 2017). Most studies targeting mTOR in cancer cells have focused on the allosteric inhibitors (rapamycin and its analogs, or "rapalogs"), which only partially block mTORC1 and do not inhibit mTORC2 due to a negative feedback on insulin/PI3K/Akt signaling. To overcome these limitations, new ATP competitive inhibitors of mTOR have been developed to blocking mTORC1 and mTORC2 simultaneously, including AZD 2014 and TAK228 (Pike et al., 2013; Rubens et al., 2017). However, inhibition of the mTORC1/2 alone has proven to be insufficient for tumor treatment, due to the induction of autophagy that promotes cancer cell survival (Saxton and Sabatini, 2017).

ATG4B is a cysteine proteases that converts LC3 to LC3-I/II, which is essential to activate autophagy (Li et al., 2011). The importance of ATG4B in normal development and disease has been demonstrated using Atg4b knockout mouse models, which have showed ATG4B deficiency as causing systemic reductions in autophagic activity (Cabrera et al., 2013; Marino et al., 2010; Read et al., 2011). An increasing amount of evidence have suggested that ATG4B is elevated in certain types of cancer, implying that ATG4B is a potential anticancer target. In cancer, ATG4B has been implicated as a biomarker and potential therapeutic target (Akin et al., 2014; Liu et al., 2014; Rothe et al., 2014; Yang et al., 2018). In patient-derived glioma stem-like cells (GSC or glioma initiating cells, GIC), we found that ATG4B is phosphorylated at serine residue 383 (p-S383) at serine residue 383, which stimulates ATG4B activity and increases autophagic flux. Inhibition of ATG4B activities using genetic approaches or an inhibitor of ATG4B, NCI Developmental Therapeutics compound NSC185058, suppresses autophagy and the tumorigenicity of glioblastoma (GBM) cells. Furthermore, inhibiting ATG4B in combination with radiotherapy (RT) in treating mice with intracranial GBM xenograft markedly slows tumor growth and provides a significant survival benefit (Huang et al., 2017).

Example 1: Materials and Methods

Cell Culture.

Glioma cells U87 (from ATCC) were cultured in DMEM (Invitrogen) supplemented with 10% FBS and 1% penicillin and streptomycin. Neural progenitor cells were cultured in NPBM Neural Progenitor Basal medium supplemented with hEGF, hFGF, NSF-1 and GA (Lonza, Cat #: cc-3210, cc-4241 and cc-4242). Patient-derived glioma spheres were previously characterized (Mao et al., 2013; Srikanth et al., 2013) were cultured in in DMEM/F12 medium containing B27 supplement (Invitrogen), penicillin and 1% streptomycin (Invitrogen), Heparin (Sigma-Aldrich), EGF, and bFGF (Peprotech).

Xenograft Studies.

Athymic (Ncr nu/nu) mice at 6-8 week age were obtained from Taconic Farms. All experiments using animals was conducted under the approved protocol by the Institutional Animal Care and Use Committees, and the Human Subjects Research protocols were approved by the Institutional Review Board at the Northwestern University. The GSC suspension ($5\times10^3$ cells for GSC 83, $5\times10^5$ cells for JK83 and GBM39) was intracranially injected into the brains of individual mice as described previously (Huang et al., 2016b). When Bioluminescent imaging (BLI) was detected in all animal, which were randomized into different treatment groups. The NSC185058 was administered on Monday, Wednesday, and Friday for two to three weeks. The radiation groups received radiation at 2 Gy for five consecutive days. TMZ-treated mice received TMZ through gavage at 100 mg/kg daily. The AZD2014 group received treatment for five consecutive days a week. The drug or radiation treatment was started one week after transplantation. Mice were monitored every day until the onset of neurological symptoms due to tumor burden. The tumor growth was monitored using the bioluminescent imaging (BLI) station (Caliper Life Sciences). Two hours after last treatment, one mouse from each group was sacrificed, mouse brain was removed and embedded in O.C.T compound (Thermal Fisher), and stored at −80° C. and subsequently processed for Immunofluorescent staining.

Pharmacokinetic Studies in Mice.

Athymic (Ncr nu/nu) mice were injected intraperitoneal (i.p.) with peanut oil vehicle or ATG4B antagonists NSC185058 (50 mg/kg body weight for high does group and 10 mg/kg body weight for low does group). Mouse blood was withdrawn by terminal cardiac puncture while the animals were anesthetized with isoflurane. Blood samples were collected in tubes containing K2EDTA as the anticoagulant at 5, 15, and 30 minutes; 1, 2, 4, 8, and 24 hours post-dose for treatment groups. Mouse brain and liver tissue were also collected from the study animals at 1, 2, 4, and 8 hours post-dose. Control group animals were sacrificed at 24 hours after vehicle injection. Blood samples were centrifuged within one hour of collection and plasma was frozen at approximately −80° C. until analyzed at for concentration of the drug. Total concentrations of the NSC185058 compound in the plasma, the liver, and the brain were measured by LC-MS/MS at Illinois Institute of Technology Research Institute.

Toxicity Evaluation of NSC185058 in Mouse Organs.

Mice were randomized into two groups before the start of experiment. Animals received peanut oil vehicle (control) or ATG4B antagonists NSC185058 (150 mg/kg body weight) on Monday, Wednesday, and Friday for tow to three weeks. Then, mouse tissues and organs including the liver, the kidney, the lung, the spleen, the heart, and the brain were collected after one week post last dose. All specimens were immediately formalin-fixed for 24-36 hrs and then embedded in paraffin embedded. Five micrometer-thick serial sections were obtained from each samples for standard hematoxylin and eosin staining.

Immunoblotting (IB).

IB assays were performed as previously described (Huang et al., 2016b). Specific antibodies were used according to the manufacturer's instructions: LC3B (#3868S), pAKT (Ser473; 4060), pAKT(Thr308; 4056), AKT (4691), pS6 (S235/236; 2211), S6 (2317), phosphorylated 4E-binding protein 1 (p4EBP1) (Thr37/46; 2855), 4EBP1 (9644), p-mTOR (Ser2448; 2971S), p-mTOR (Ser2481; 2974S), mTOR (2972S), pULK1(Ser317; 14202T), pULK1 (Ser757; 8054T), ULK1(6439), LAMP2 (49067S) were from Cell Signaling Technology. Anti-β-actin (SC-47778) and anti-SQSTM1/p62 (SC-28359) antibodies were from Santa Cruz Biotechnology. An anti-Ki-67 antibody (AB9260) was from EMD Millipore.

Immunofluorescent staining. GSCs were seeded onto LabTek CC2-treated tissue culture slides (Thermo Fisher) and cultured for 24 hours. Cells were then fixed with 4% formaldehyde (Fisher) for 15 min, and permeabilized with 0.1% Triton X-100, and then blocked with AquaBlock (East Coast Bio, North Berwick, Me.) for 60 minutes. The slides were incubated with indicated primary antibodies according to the manufacturer's instructions. After being washed for three times with PBS-T, cells were incubated with secondary antibody (Alexa 488 and 594, 1:200) and DAPI-containing mounting solution Vectashield (Vector Laboratories). Cells were analyzed on a Nikon inverted microscope Eclipse Ti-U equipped with a digital camera.

Frozen brain tissue sections with GBM xenografts were dried and then fixed in were fixed in 4% paraformaldehyde (PFA) in PBS for 5 minutes. Tissue sections were blocked with AquaBlock (East Coast Bio, North Berwick, Me.) for an hour and then were probed with appropriate primary antibodies 4° C. overnight. Tissue sections were incubated with Alexa 488 or 594 labelled secondary antibodies (1:200) and DAPI-containing mounting solution Vectashield (Vector Laboratories), and representative images were photographed using a Nikon inverted microscope Eclipse Ti-U equipped with a digital camera.

Cell Viability Assay.

GSCs with single or combined treatments were cultured for 72 hours in 96-well plates at 2,000 cells per well. Cell viabilities were determined using CellTiter-Glow 2.0 Assay (Promega).

Cell Growth Assay.

In vitro cell growth assay was conducted as previously described (Huang et al., 2016a). Briefly, cell density was quantified by counting viable, Trypan Blue negative cells using a hematocytometer. 10,000 cells were seed into each well of 6-well plate containing 2 ml culture medium. The number for living cells was counted at 72 hrs after indicated treatment using a hematocytometer.

Cell Apoptosis Assay.

Cells undergoing apoptosis were washed and incubated in 500 μl binding buffer, 5 μl annexin V-FITC and 5 μl of propidium iodide (PI) (Invitrogen) in the dark at room temperature for 15 min. Samples were analyzed by flow cytometry (Millipore guava EasyCyte flow cytometer). The percentage of Annexin V positive cells was recorded as the indicator of apoptosis intensity.

Statistical Analysis.

Statistical analysis was conducted using Microsoft Excel 2013 and Prism 6.0 (GraphPad Inc.). Analysis included one-way ANOVA with Newman-Keuls post-test and paired two-way Student t-test. The statistical significance of Kaplan-Meier survival plot was determined by log-rank analysis.

Figure 1:
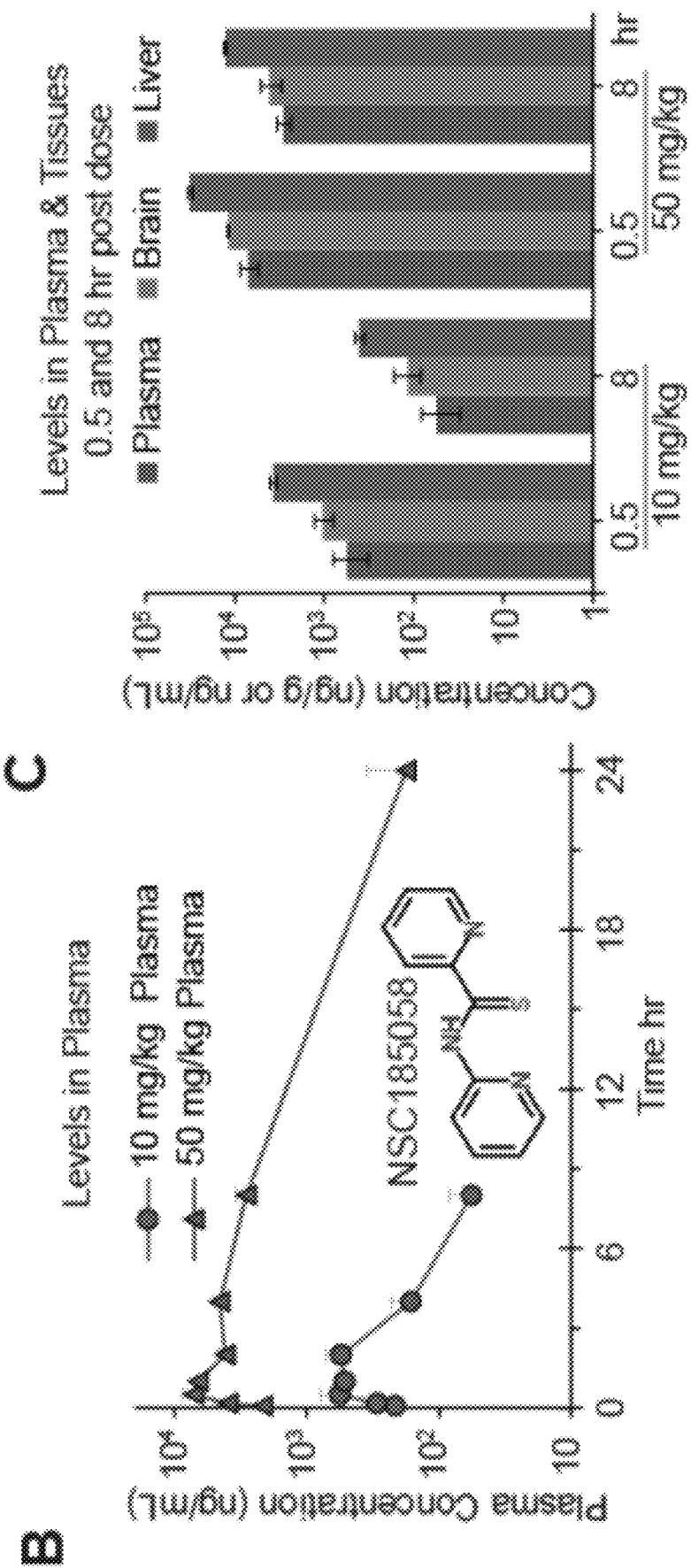
FIG. 1. NSC185058 (NSC) effectively distributes to the plasma, the brain, and the liver with minimal toxicity in mice. (A) to (C) Mice were dosed with peanut oil vehicle or ATG4B antagonists NSC185058 at doses of 10 or 50 mg/kg body weight. Plasma, the brain, and the liver tissues were collected at the indicated time points. (A) Total concentrations of the NSC compound in plasma were measured by LC-MS/MS. The PK parameter of NSC in plasma was determined. (B) NSC levels in plasma were determined form 5 min to 24 hr post dosing. The chemical structure of NSC was shown. (C) NSC levels were determined in the plasma, the brain, and the liver tissues at 0.5 and 8 hr post dosing. (D) Hematoxylin and eosin stained section s of indicated organs that were treated with NSC (150 mg/kg body weight) or vehicle on Monday, Wednesday, and Friday for three weeks. Scale bars, 50 µm. n=3 mice/group/time point.
Figure 1:
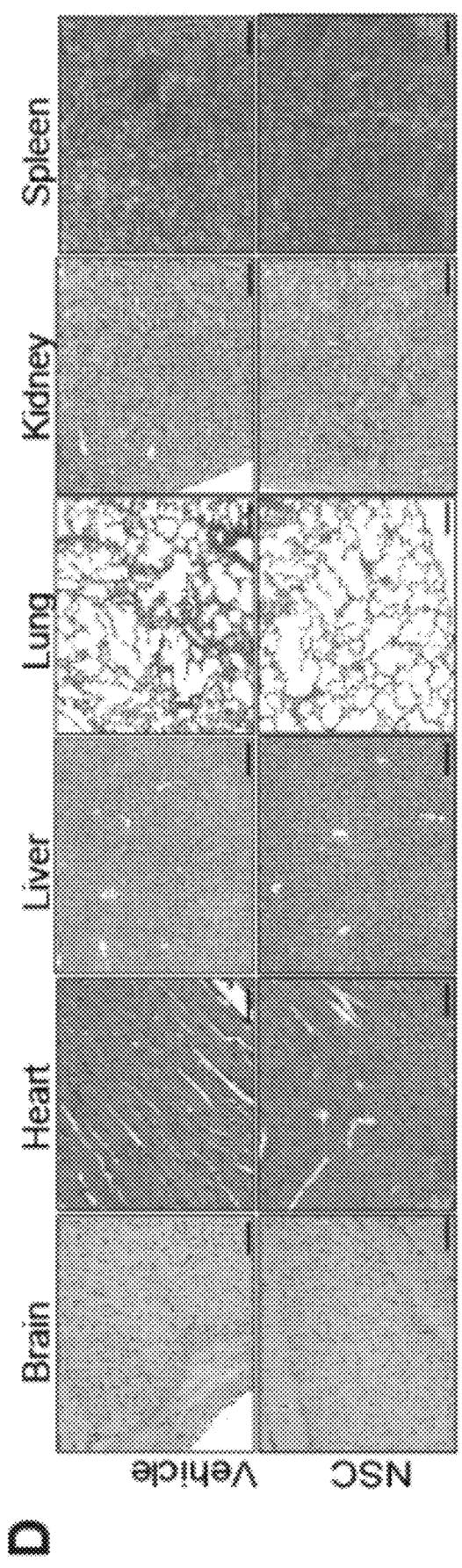

Example 2: NSC18058 Maintains Effective Levels with Comparative Distribution in the Plasma, the Brain, and the Liver, and Exhibit Minimal Toxicity in Mice The NSC was administered at the dose of 10 or 50 mg/kg body weight in group of three mice. At the indicated time points spanning a 24 hrs period (5, 10 min, 0.5, 1, 2, 4, 8, and 24 hour), the plasma, the brain, and the liver tissues were collected. Plasmid and extracts from the brain and the liver were analyzed by LC-MS/MS using method developed at the Illinois Institute of Technology Research Institute (IITRI). As shown in FIGS. 1A and 1B, average maximum plasma concentration (Cmax) after IP single doses at 10 or 50 mg/kg dose group 2.6 and 33 μM, respectively. Area under the curve (AUC) for the plasma collected from receiving 10 and 50 mg/kg dose group were 2,135 and 57,248 hr*ng/ml, respectively. Plasma exposure appears to increase beyond the hinge in dose for the dosing range tested. The elimination half-life was 2 and 4 for the 10 and 50 mg/kg dose, respectively. The NSC compound distributes well to the brain with average tissue concentration of 40 to 100% that was observed in the plasma at the same time points (FIG. 1C). Average brain tissue concentration for 50 mg/kg dose was 11951 and 4098 ng/g at the 0.5 and 8 hrs post IP dose, indicating that NSC penetrates the tumor blood-brain barrier at sufficient levels. To examine whether NSC is tolerated in mouse, we investigated the effect induced by NSC in mouse behavior or by pathologic analysis of vital organs including the brain, the heart, the liver, the lung, the kidney, and the spleen. Mice underwent treatments on Monday, Wednesday, and Friday for three week with either peanut oil (vehicle) or NSC (150 mg/kg body weight) in peanut oil. The mice did not display behavioral changes. Animal tissues were collected one week after the last dosing and subject for hematoxylin and eosin staining. As shown in FIG. 1D, there are no morphological changes or abnormal findings in retrieved tissues, indicating NSC is not a toxic agent that pose acute toxicity or inflammation for animal, even the dose of three fold higher than that was selected to investigate its effect on the growth of xenograft tumor.

Figure 2:
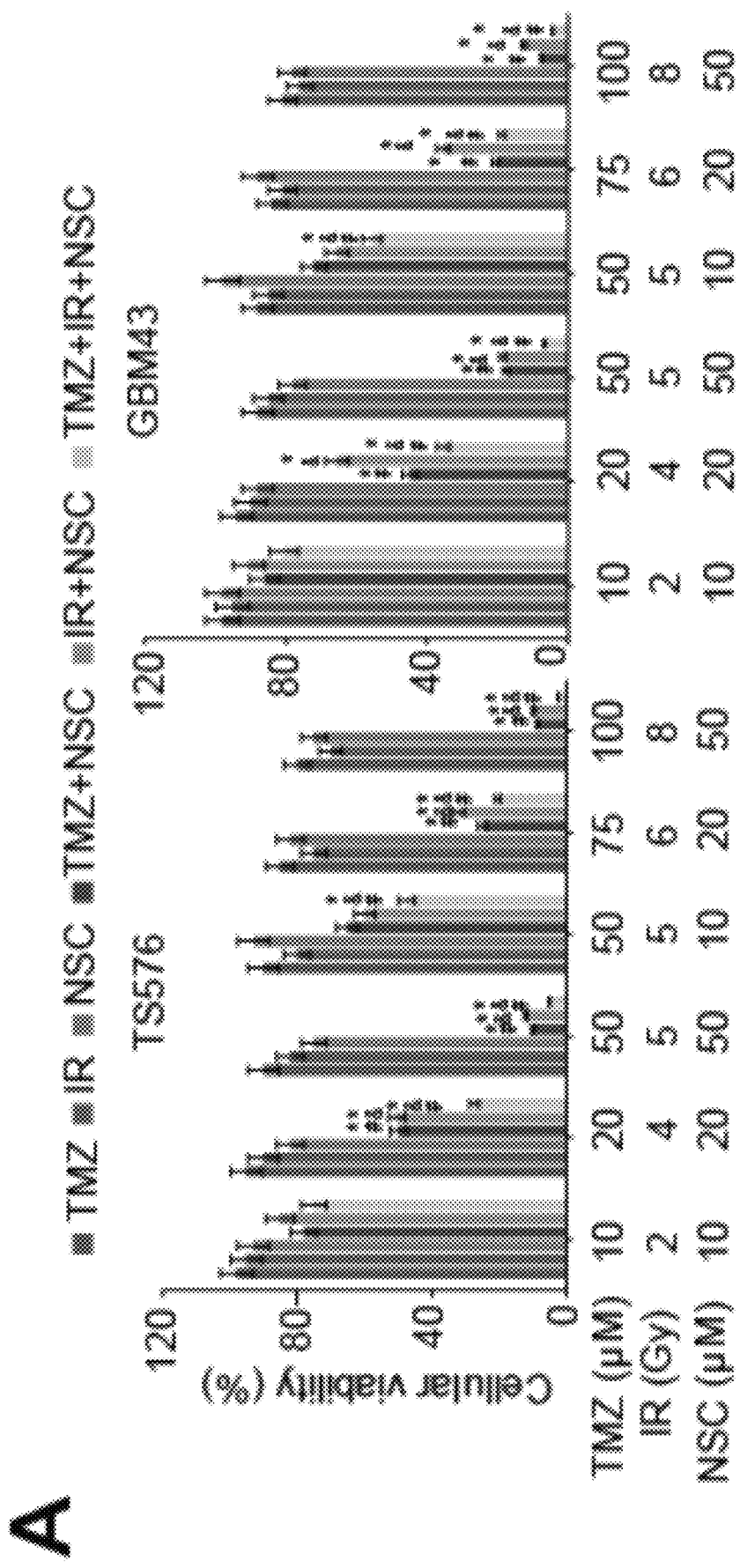
FIG. 2. Combination of NSC and Irradiation (IR) or/and TMZ Results in Synergistic Growth Inhibition of GSCs and Patient-derived Xenograft (PDX) GBM Cells. (A) GBM stem-like cells, GSCTS576, and patient-derived xenograft cells, GBM44, were treated with NSC, IR or/and TMZ at the indicated concentrations and combinations for 72 hours. Thereafter, cells were analyzed for cellular viability. Data are shown as mean±SD, n=3 of biological replicates. #, Combination vs. TMZ, P<0.01; &, Combination vs. IR, P<0.01; *, Combination vs. NSC, P<0.01 (B) GSCTS576 and GBM44 cells were treated with NSC, IR or and TMZ with indicated concentration or does for 48 hours, stained with Annexin V/PI, and analyzed by flow cytometry; n=3 biological replicates. Data are shown as mean±SD. #, Combination vs. TMZ, P<0.01; &, Combination vs. IR, P<0.01; *, Combination vs. NSC, P<0.01. (C) TS576 GSCs and GBM44 with indicated treatments were collected and analyzed for levels of the indicated proteins. Cleaved CASP3/ caspase-3: Apoptosis indicator; γH2AX: DNA damage indicator; LC3B and p62/SQSTM1, autophagy indicators.
Figure 2:
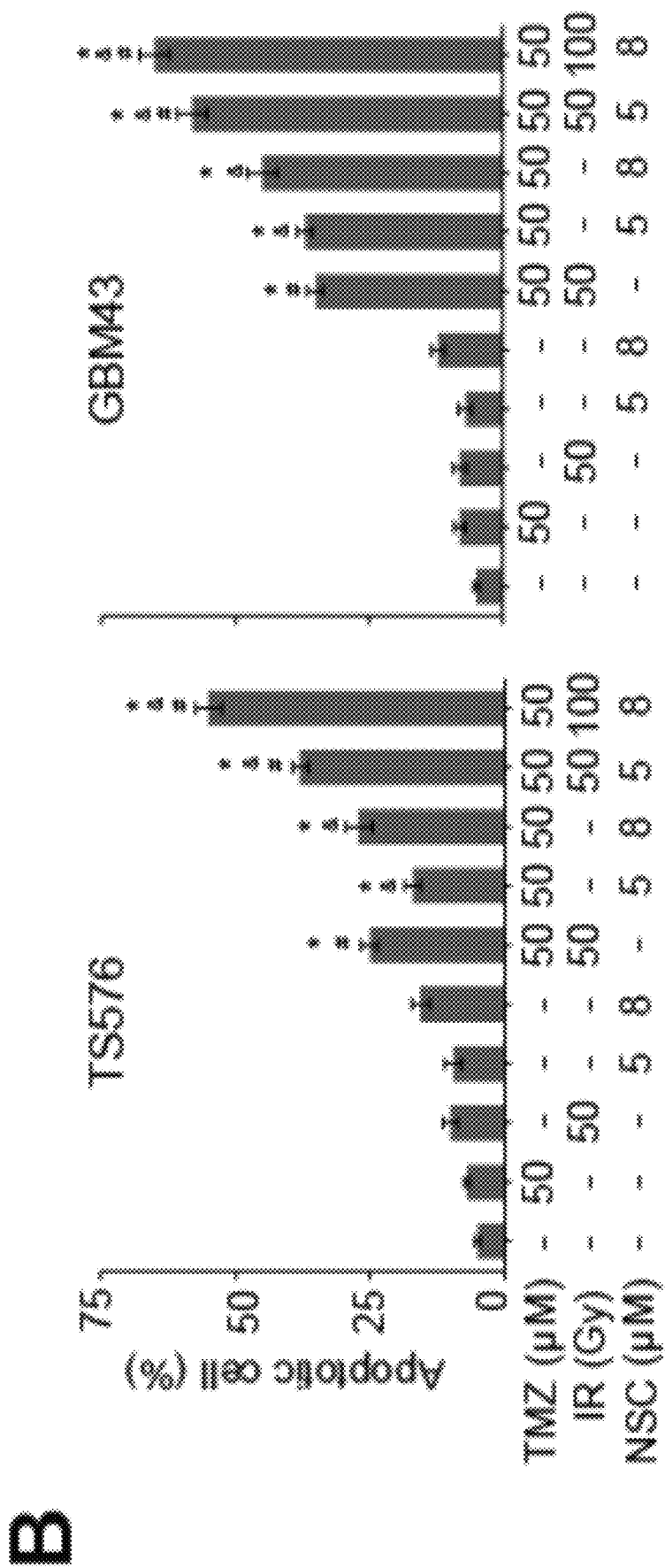
Figure 2:
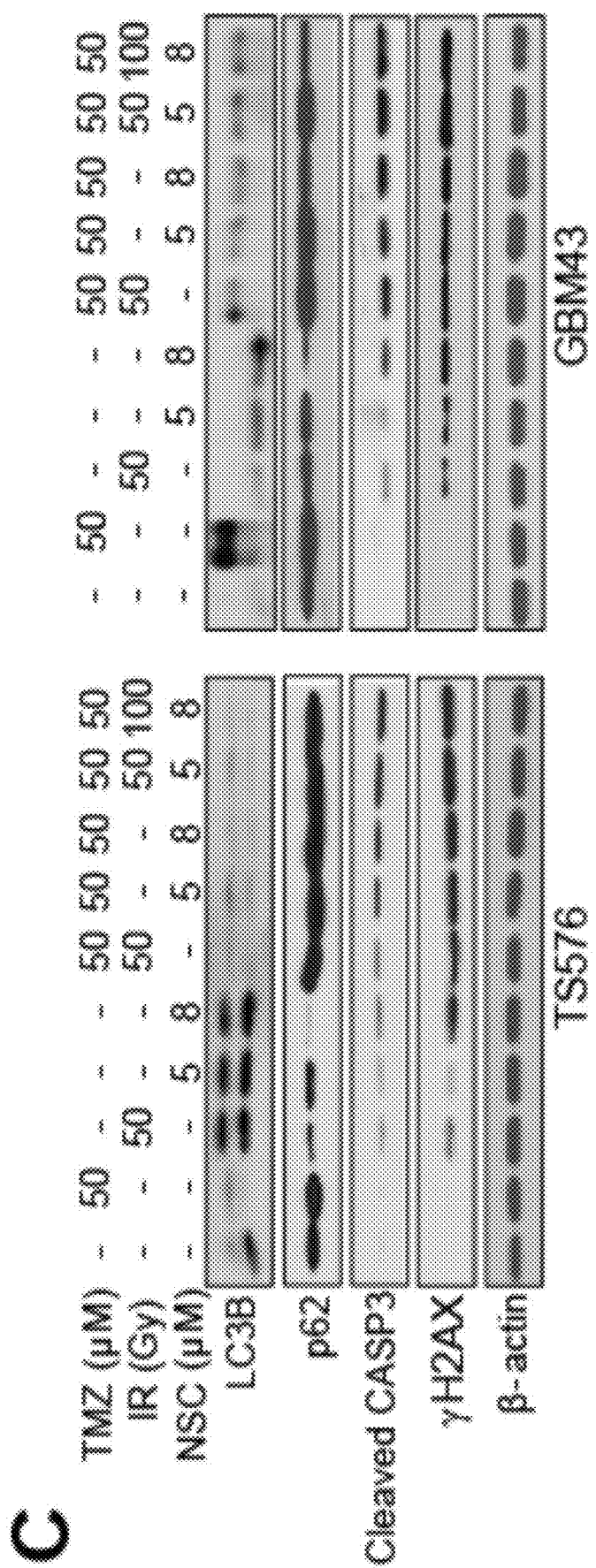

Example 3: Combination of NSC185058 and Irradiation (IR) or/and TMZ Elicits Synthetic Lethality in Glioblastoma RT and TMZ are the first-line treatments for many types of cancers including GBM. Tumor cells employed autophagy as a resistance mechanism in response to RT and TMZ (Janku et al., 2011; Zhang et al., 2015). To determine the effect of combination treatment with NSC185058 and irradiation (IR) or/and TMZ, stem-like glioma cells (GSC83) and patient-derived xenograft GBM (GBM43) cells, were treated with NSC185058, TMZ, IR or the combination of two or three treatments and examined cellular proliferation modulation. Consistently, the combination treatment of NSC and IR or/and TMZ led to more reduction in tumor cell proliferation cells than single treatments (FIG. 2A). The combination of NSC and IR or/and TMZ resulted in morphological signs of apoptosis. To determine as to whether or not features of apoptotic cell death can be confirmed biochemically, GSC83 and GBM43 cells with treatment of NSC, IR, TMZ, or the combination of both or all were stained with Annexin V/propidium iodide and analyzed by multiparametric flow cytometric analysis. Consistently, we found that the combination treatment of NSC+ IR or/and TMZ led to more apoptotic cells than single treatments (FIG. 2B). Given the activation of apoptosis, it is considered about the cell death induction by the combination treatment is through suppression of cellular autophagy. Toward this end, we analyzed protein expression of autophagy marker protein LC3B and p62/SQSTM1, an established autophagy substrate, DNA damage indicator γH2AFX/γH2AX and apoptosis indicator cleaved CASP3/caspase-3 in both tested cell lines. The results were revealed that IR or TMZ induced autophagy in GSCs and GBM cells as indicated by increased LC3B lipidation and p62 breakdown (FIG. 2C). Inhibition of ATG4B by NSC treatment sensitized the tested cells to IR or/and TMZ by suppressing LC3B lipidation and increasing p62.

For analysis of in vivo effects of NSC, IR and TMZ, mice with intracranial GSC or PDX GBM xenografts with modification for luciferase expression, received intraperitoneal injection of NSC at 150 mg/kg on Monday, Wednesday, and Friday, for two or three weeks, with IR (5×2 Gy daily or/TMZ at the dose of 100 mg/kg of mouse body weight for two or three weeks (FIGS. 3A and 4A). All monotherapy showed a moderate growth-suppressive effect on intracranial tumors of GSC 83, while only TMZ monotherapy had marked suppression on the growth of intracranial PDX GBM39 tumors, as indicated by mouse body weight and bioluminescence monitoring of tumor response to treatment (FIGS. 3B to 3D and 4B to 4D). However, survival analysis showed that IR, TMZ rather than NSC produced survival benefit to intracranial GSC83 xenografts (FIG. 3F), while only monotherapy of TMZ, but not IR or NSC single treatment resulted in growth-suppressive effects on intracranial PDX GBM39 tumor xenografts (FIG. 4E). Notably, all combination treatments showed significantly increased antitumor activity for intracranial GSC83 xenografts, relative to monotherapy, with co-administration of IR, TMZ and TMZ regimens performing the best (FIG. 3B-3F). Similar effects of combined treatments of NSC, IR or/TMZ on growth of intracranial tumors were also found in PDX GBM39 models in vivo in which tri-treatment showed the most significant synergistic interaction (FIG. 4B-4E).

Example 4: NSC185058 Enhances Anti-Tumor Activity of AZD2014 in Glioblastoma (GBM)

mTOR kinases are crucial regulators of glioma cell growth, proliferation and survival (Akhavan et al., 2010). AZD2014 is a novel mTOR kinase inhibitor that inhibits both mTORC1 and mTORC2 complexes, and showed a greater inhibitory ability to block mTORC1 than the clinically approved rapalogs (Guichard et al., 2015). To test the potential role of AZD2014 on glioma cell survival, cell viability assay was performed, and results demonstrated that AZD2014 significantly decreased cell viability of U87 cells at the concentration of 0.1 µM and that of GSC JK83 and M83 at 1 µM (FIG. 5A), and the inhibition efficiency of AZD2014 on GSCs was significantly lower than glioma cells under the same concentration of AZD2014, indicating that GSCs are comparatively more resistance to mTOR inhibition, in relation to U87 cells, which are in differentiated state. The inhibitory effects of AZD2014 on mTORC1 and mTORC2 activity were determined in GSC M83 and JK83 cells, and results demonstrated that AZD2014 dose-dependently inhibited p-S6, p-4EBP1, and p-AKT (Ser473). A strong inhibition was achieved by 1 µM with complete block of mTORC1/2 activities at 2 µM (FIG. 5B). To further determine mTOR inhibition as a function of time after exposure to AZD2014, GSC M83 and JK83 were treated with AZD2014 and results showed that inhibition of mTORC1 and mTORC2 was detectable by 2 hrs. Notably, a consequence of mTOR inhibition is autophagy induction. Immunoblotting results revealed that AZD2014 increased LC3-II conversion (LC3B-II/I ratio) and p62/SQSTM-1 degradation, an established autophagy substrate (FIG. 5B). Together, these results indicate that AZD2014 blocks mTORC1/2 activation and simultaneously induces autophagy that may serve as a resistance factor in GSCs.

Since autophagy activation is considered as a cytoprotective factor that contribute to tumor survival when challenged by therapies, it is proposed that block of autophagy activation by NSC would further enhanced the cytotoxicity of dual TORC1/2 inhibitor AZD2014. In GSC83 and JK83 cells, AZD2014 inhibited mTOR induced p-52448/81-mTOR, p-S473-Akt, p-S6, p-S757-ULK1, but also induced autophagic influx by inducing LC3B lipidation and degradation of p62 and LAMP2 (FIG. 6A), a lysosomal membrane protein that is essential for lysosome biogenesis and autophagy (Eskelinen, 2006). These results suggest that inhibition of mTOR induced autophagy through depression of ULK1. Inclusion of NSC attenuated autophagy induction by suppressing ATG4B-mediated LC3B conversation, as well as p62 and LAMP2 degradation without affecting the mTOR signaling and ULK1 activity (FIG. 6A). The results of LC3 B immunofluorescence showed an increase of autophagosomes number in the GSC M83 and JK83 cells treated with AZD2014, but markedly decreased with NSC (FIG. 6B). Furthermore, combined NSC and AZD2014 markedly decreased cell viability, and induced significantly higher rates of apoptosis compared with monotherapy with AZD2014 or NSC (FIGS. 6C and 6D). These results indicate that autophagy inhibition enhances the in vitro sensitivity of GSCs to dual mTOR inhibition, although AZD2014 alone displayed inhibitor effects on GBM cell viability.

To determine whether the enhancement of AZD2014 therapeutic efficiency by combination with NSC measured in vitro extends to an orthotopic model, GSC JK83 glioma spheres were employed to initiate intracerebral xenografts in mice. Both NSC (100 mg/kg) and AZD2014 (50 mg/kg) treatment alone had modest but significant effects on mouse survival when compared with control treatment. The survival time of animals receiving the combination treatment (AZD2014+NSC) was significantly increased when compared to control (FIGS. 7A and 7B), indicating that NSC enhanced the inhibition efficiency of AZD2014 on the growth of orthotopic xenografts initiated from patient-derived GSCs. Immunofluorescent histochemical analysis of tumor tissues upon completion of treatment showed that AZD2014 treatment significantly reduced in the levels of p-4EBP1 and p-AKT in the group of AZD2014 alone or in combination with NSC when compared to control. Inhibition of autophagy by NSC (50 mg/kg) had a slight impact on autophagic flux (by LC3B puncta staining) in brain tumor xenografts from the group of NSC alone, and strongly attenuated AZD2014-induced autophagy response in the brain of mice receiving the combination protocol (FIG. 7C). Furthermore, the group treated with a combination of AZD2014 and NSC had significantly lower proliferation index (by Ki-67 staining) when compared to the group of AZD or NSC alone (FIG. 7C). Taken together, these results indicated that suppression of autophagy by NSC enhances AZD2014 cytotoxicity in vivo, and inhibition of autophagy provided greater than additive effect on survival compared with the survival benefit of the AZD2014 treatments alone.

Example 5—Effects of NSC185058 (NSC), Irradiation (IR), and Temozolomide (TMZ) in Mice with Intracranial PDX GB6FL We further determined in vivo effects of NSC, IR, and TMZ on mice with intracranial PDX GBM6FL temozolomide (TMZ) resistant (res) xenografts with modification for luciferase expression. GBM6FL TMZ res orthotopic xenograft model was recently established by Dr. Charles David James at Northwestern University as intracranial GBM xenografts after three runs of TMZ treatments and subsequent passages in the flanks of mice. These intracranial GBM6FL TMZ res glioma xenografts exhibited no response in vivo to TMZ treatments compared to vehicle-treated brain xenografts (controls). Mice with intracranial GBM6FL TMZ res xenografts received intraperitoneal injection of NSC at 150 mg/kg of mouse body weight on Monday, Wednesday, and Friday, for three weeks (post-implantation days 7 to 28), with IR (2 Gy daily for 5 days) or/TMZ at the dose of 100 mg/kg of mouse body weight for three weeks (post-implantation days 7 to 28, FIG. 8A). All monotherapy and dual therapy of TMZ, IR and/or NSC showed a minimal growth-suppressive effect on intracranial tumors of GBM6FL TMZ res, while only triple combination therapy (IR+TMZ+NSC) had marked suppression on the growth of intracranial GBM6FL TMZ res tumors, as indicated by mouse body weight and bioluminescence monitoring of tumor response to treatment (FIGS. 8B to 8D). Survival analysis showed that triple combination therapy (IR+TMZ+NSC) produced appreciable survival benefit to intracranial GBM6FL TMZ res xenografts, but none of monotherapy or dual therapy of TMZ, IR, and/or NSC showed significant increase in antitumor activity, relative to control (FIGS. 8E and 8F). This data suggest the utility of triple combination therapy of IR, TMZ, and NSC in improving GBM response to treatments of TMZ and IR+TMZ.

REFERENCES

[1] Akhavan, D., Cloughesy, T. F., and Mischel, P. S. (2010). mTOR signaling in glioblastoma: lessons learned from bench to bedside. Neuro-oncology 12, 882-889.

[2] Akin, D., Wang, S. K., Habibzadegah-Tari, P., Law, B., Ostrov, D., Li, M., Yin, X. M., Kim, J. S., Horenstein, N., and Dunn, W. A., Jr. (2014). A novel ATG4B antagonist inhibits autophagy and has a negative impact on osteosarcoma tumors. Autophagy 10, 2021-2035.

[3] Amaravadi, R., Kimmelman, A. C., and White, E. (2016). Recent insights into the function of autophagy in cancer. Genes & development 30, 1913-1930.

[4] Cabrera, S., Fernandez, A. F., Marino, G., Aguirre, A., Suarez, M. F., Espanol, Y., Vega, J. A., Laura, R., Fueyo, A., Fernandez-Garcia, M. S., et al. (2013). ATG4B/autophagin-1 regulates intestinal homeostasis and protects mice from experimental colitis. Autophagy 9, 1188-1200.

[5] Deretic V, Saitoh T, Akira S. Autophagy in infection, inflammation and immunity. Nat Rev Immunol. 2013; 13(10):722-737. PMID: 24064518.

[6] Eskelinen, E. L. (2006). Roles of LAMP-1 and LAMP-2 in lysosome biogenesis and autophagy. Molecular aspects of medicine 27, 495-502.

[7] Galluzzi L, Pietrocola F, Bravo-San Pedro J M, et al. Autophagy in malignant transformation and cancer progression. Embo J. 2015; 34(7):856-880. PMID: 25712477.

[8] Guichard, S. M., Curwen, J., Bihani, T., D'Cruz, C. M., Yates, J. W., Grondine, M., Howard, Z., Davies, B. R., Bigley, G., Klinowska, T., et al. (2015). AZD2014, an Inhibitor of mTORC1 and mTORC2, Is Highly Effective in ER+ Breast Cancer When Administered Using Intermittent or Continuous Schedules. Molecular cancer therapeutics 14, 2508-2518.

[9] Huang, T., Alvarez, A. A., Pangeni, R. P., Horbinski, C. M., Lu, S., Kim, S. H., James, C. D., J, J. R., J, A. K., Brenann, C. W., et al. (2016a). A regulatory circuit of miR-125b/miR-20b and Wnt signalling controls glioblastoma phenotypes through FZD6-modulated pathways. Nature communications 7, 12885.

[10] Huang, T., Kim, C. K., Alvarez, A. A., Pangeni, R. P., Wan, X., Song, X., Shi, T., Yang, Y., Sastry, N., Horbinski, C. M., et al. (2017). MST4 Phosphorylation of ATG4B Regulates Autophagic Activity, Tumorigenicity, and Radioresistance in Glioblastoma. Cancer Cell 32, 840-855 e848.

[11] Huang, T. Z., Alvarez, A. A., Pangeni, R. P., Horbinski, C. M., Lu, S. J., Kim, S. H., James, C. D., Raizer, J. J., Kessler, J. A., Brenann, C. W., et al. (2016b). A regulatory circuit of miR-125b/miR-20b and Wnt signalling controls glioblastoma phenotypes through FZD6-modulated pathways. Nature Communications 7:12885.

[12] Huang T. Z., Wan X., Alvarez A. A., James C. D., Song X., Yang Y., Sastry N, Nakano I., Sulman E. P. Hu B., and Cheng S.-Y. (2019) MIR93 (microRNA-93) regulates tumorigenicity and therapy response of glioblastoma by targeting autophagy June; 15(6):1100-1111. doi: 10.1080/15548627.2019.1569947. Epub 2019 Jan. 31.

[13] Janku, F., McConkey, D. J., Hong, D. S., and Kurzrock, R. (2011). Autophagy as a target for anticancer therapy. Nature reviews Clinical oncology 8, 528-539.

[14] Kabeya Y, Mizushima N, Yamamoto A, et al. LC3, GABARAP and GATE16 localize to autophagosomal membrane depending on form-II formation. J Cell Sci. 2004; 117(Pt13):2805-2812. PMID: 15169837.

[15] Kang R, Zeh H J, Lotze M T, et al. The Beclin 1 network regulates autophagy and apoptosis. Cell Death Differ. 2011; 18(4):571-580. PMID: 21311563.

[16] Kondo Y, Kanzawa T, Sawaya R, et al. The role of autophagy in cancer development and response to therapy. Nat Rev Cancer. 2005; 5(9):726-734. PMID: 16148885.

[17] Kroemer G. Autophagy: a druggable process that is deregulated in aging and human disease. J Clin Invest. 2015; 125(1):1-4. PMID: 25654544.

[18] Lee Y, Chou T F, Pittman S K, et al. Keap1/Cullin3 modulates p62/SQSTM1 activity via UBA domain ubiquitination. Cell Rep. 2017; 20(8):1994 PMID: 28834760.

[19] Levine, B., and Kroemer, G. (2008). Autophagy in the pathogenesis of disease. Cell 132, 27-42.

[20] Li, M., Hou, Y., Wang, J., Chen, X., Shao, Z. M., and Yin, X. M. (2011). Kinetics comparisons of mammalian Atg4 homologues indicate selective preferences toward diverse Atg8 substrates. The Journal of biological chemistry 286, 7327-7338.

[21] Liu B, Bao J K, Yang J M, et al. Targeting autophagic pathways for cancer drug discovery. Chin J Cancer. 2013; 32(3):113-120. PMID: 22835386.

[22] Liu, P. F., Leung, C. M., Chang, Y. H., Cheng, J. S., Chen, J. J., Weng, C. J., Tsai, K. W., Hsu, C. J., Liu, Y. C., Hsu, P. C., et al. (2014). ATG4B promotes colorectal cancer growth independent of autophagic flux. Autophagy 10, 1454-1465.

[23] Mao, P., Joshi, K., Li, J., Kim, S. H., Li, P., Santana-Santos, L., Luthra, S., Chandran, U. R., Benos, P. V., Smith, L., et al. (2013). Mesenchymal glioma stem cells are maintained by activated glycolytic metabolism involving aldehyde dehydrogenase 1A3. Proceedings of the National Academy of Sciences of the United States of America 110, 8644-8649.

[24] Marino, G., Fernandez, A. F., Cabrera, S., Lundberg, Y. W., Cabanillas, R., Rodriguez, F., Salvador-Montoliu, N., Vega, J. A., Germana, A., Fueyo, A., et al. (2010). Autophagy is essential for mouse sense of balance. The Journal of clinical investigation 120, 2331-2344.

[25] Mizushima N, Komatsu M. Autophagy: renovation of cells and tissues. Cell. 2011; 147(4):728-741. PMID: 22078875. [PubMed] [Google Scholar]

[26] Pike, K. G., Malagu, K., Hummersone, M. G., Menear, K. A., Duggan, H. M., Gomez, S., Martin, N. M., Ruston, L., Pass, S. L., and Pass, M. (2013). Optimization of potent and selective dual mTORC1 and mTORC2 inhibitors: the discovery of AZD8055 and AZD2014. Bioorganic & medicinal chemistry letters 23, 1212-1216.

[27] Pyo J O, Nah J, Jung Y K. Molecules and their functions in autophagy. Exp Mol Med. 2012; 44(2):73-80. PMID: 22257882. [PMC free article] [PubMed] [Google Scholar]

[28] Rabinowitz J D, White E. Autophagy and metabolism. Science. 2010; 330(6009):1344-1348. PMID: 21127245. [PMC free article] [PubMed] [Google Scholar]

[29] Read, R., Savelieva, K., Baker, K., Hansen, G., and Vogel, P. (2011). Histopathological and neurological features of Atg4b knockout mice. Veterinary pathology 48, 486-494.

[30] Rothe, K., Lin, H., Lin, K. B., Leung, A., Wang, H. M., Malekesmaeili, M., Brinkman, R. R., Forrest, D. L., Gorski, S. M., and Jiang, X. (2014). The core autophagy protein ATG4B is a potential biomarker and therapeutic target in CML stem/progenitor cells. Blood 123, 3622-3634.

[31] Rubens, J. A., Wang, S. Z., Price, A., Weingart, M. F., Allen, S. J., Orr, B. A., Eberhart, C. G., and Raabe, E. H. (2017). The TORC1/2 inhibitor TAK228 sensitizes atypical teratoid rhabdoid tumors to cisplatin-induced cytotoxicity. Neuro-oncology 19, 1361-1371.

[32] Saxton, R. A., and Sabatini, D. M. (2017). mTOR Signaling in Growth, Metabolism, and Disease. Cell 168, 960-976.

[33] Srikanth, M., Das, S., Berns, E. J., Kim, J., Stupp, S. I., and Kessler, J. A. (2013). Nanofiber-mediated inhibition of focal adhesion kinase sensitizes glioma stemlike cells to epidermal growth factor receptor inhibition. Neuro-oncology 15, 319-329.

[34] White E. The role for autophagy in cancer. J Clin Invest. 2015; 125(1):42-46. PMID: 25654549. [PMC free article] [PubMed] [Google Scholar]

[35] Xie Z, Klionsky D J. Autophagosome formation: core machinery and adaptations. Nat Cell Biol. 2007; 9(10): 1102-1109. PMID: 17909521.

[36] Yang, A., Herter-Sprie, G., Zhang, H., Lin, E. Y., Biancur, D., Wang, X., Deng, J., Hai, J., Yang, S., Wong, K. K., and Kimmelman, A. C. (2018). Autophagy Sustains Pancreatic Cancer Growth through Both Cell-Autonomous and Nonautonomous Mechanisms. Cancer discovery 8, 276-287.

[37] Zhang, D., Tang, B., Xie, X., Xiao, Y. F., Yang, S. M., and Zhang, J. W. (2015). The interplay between DNA repair and autophagy in cancer therapy. Cancer biology & therapy 16, 1005-1013.

[38] U.S. Pat. No. 8,554,841.

[39] U.S. Publication No. 2010/02859012.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating glioblastoma in a subject in need thereof, the method comprising (i) administering to the subject a therapeutic agent that inhibits the biological activity of ATG4B; (ii) administering to the subject an alkylating agent; and (iii) administering to the subject radiotherapy, wherein the glioblastoma is resistant to radiotherapy in the absence of the therapeutic agent that inhibits the biological activity of ATG4B.

2. The method of claim 1, wherein the therapeutic agent that inhibits the biological activity of ATG4B comprises a compound referred to as NSC 185058, CAS 39122-38-8, N-pyridin-2-yl-pyridine-2-carbothioamide, having the following formula or a salt thereof:

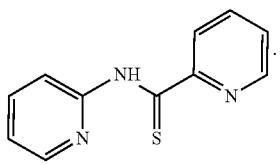 [SMILES: S=C(Nc1ccccn1)c1ccccn1]

3. The method of claim 1, wherein the therapeutic agent that inhibits the biological activity of ATG4B comprises a compound referred to as NSC 377071, CAS 26097-80-3, Novazole, Cambendazole, or Propan-2-yl N-[2-(1,3-thiazol-4-yl)-3H-benzimidazol-5-yl]carbamate, having the following formula or a salt thereof:

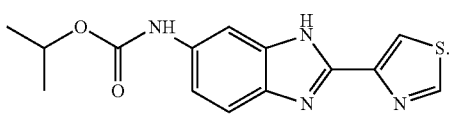 [SMILES: CC(C)OC(=O)Nc1ccc2nc(-c3cscn3)[nH]c2c1]

4. The method of claim 1, wherein the therapeutic agent that inhibits the biological activity of ATG4B comprises a compound having the following formula or a salt thereof:

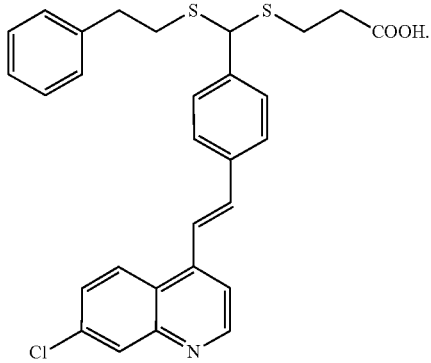 [SMILES: O=C(O)CCSC(SCCc1ccccc1)c1ccc(/C=C/c2ccnc3cc(Cl)ccc23)cc1]

5. The method of claim 1, wherein the alkylating agent is selected from temozolomide, decarbazine, altretamine, thiotepa, busulfan, carmustine, lomustine, and steptozocin, bendamustine, chlorambucil, cyclophosphamide, ifosfamide, mechlorethamine, melphalan, trabectedin, and luribectedin.

6. The method of claim 1, wherein the glioblastoma is resistant to treatment with the alkylating agent and the radiotherapy in the absence of the therapeutic agent that inhibits the biological activity of ATG4B.

7. A method for treating glioblastoma in a subject in need thereof, the method comprising (i) administering to the subject a therapeutic agent that inhibits the biological activity of ATG4B; (ii) administering to the subject an alkylating agent; and (iii) administering to the subject radiotherapy,
   wherein the glioblastoma is resistant to treatment with the alkylating agent or the radiotherapy in the absence of the therapeutic agent that inhibits the biological activity of ATG4B and
   wherein and the alkylating agent is temozolomide and the therapeutic agent that inhibits the biological activity of ATG4B comprises a compound referred to as NSC 185058, CAS 39122-38-8, N-pyridin-2-yl-pyridine-2-carbothioamide, having the following formula or a salt thereof:

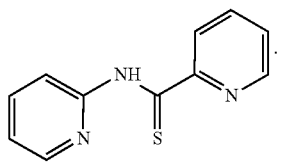 [SMILES: S=C(Nc1ccccn1)c1ccccn1]
* * * * *

SEQUENCE LISTING

```
<160> NUMBER OF SEQ ID NOS: 5

<210> SEQ ID NO 1
<211> LENGTH: 393
<212> TYPE: PRT
<213> ORGANISM: Homo sapiens

<400> SEQUENCE: 1

Met Asp Ala Ala Thr Leu Thr Tyr Asp Thr Leu Arg Phe Ala Glu Phe
1               5                   10                  15

Glu Asp Phe Pro Glu Thr Ser Glu Pro Val Trp Ile Leu Gly Arg Lys
            20                  25                  30

Tyr Ser Ile Phe Thr Glu Lys Asp Glu Ile Leu Ser Asp Val Ala Ser
        35                  40                  45

Arg Leu Trp Phe Thr Tyr Arg Lys Asn Phe Pro Ala Ile Gly Gly Thr
    50                  55                  60
```

Gly Pro Thr Ser Asp Thr Gly Trp Gly Cys Met Leu Arg Cys Gly Gln
65                  70                  75                  80

Met Ile Phe Ala Gln Ala Leu Val Cys Arg His Leu Gly Arg Asp Trp
                85                  90                  95

Arg Trp Thr Gln Arg Lys Arg Gln Pro Asp Ser Tyr Phe Ser Val Leu
            100                 105                 110

Asn Ala Phe Ile Asp Arg Lys Asp Ser Tyr Tyr Ser Ile His Gln Ile
        115                 120                 125

Ala Gln Met Gly Val Gly Glu Gly Lys Ser Ile Gly Gln Trp Tyr Gly
    130                 135                 140

Pro Asn Thr Val Ala Gln Val Leu Lys Lys Leu Ala Val Phe Asp Thr
145                 150                 155                 160

Trp Ser Ser Leu Ala Val His Ile Ala Met Asp Asn Thr Val Val Met
                165                 170                 175

Glu Glu Ile Arg Arg Leu Cys Arg Thr Ser Val Pro Cys Ala Gly Ala
                180                 185                 190

Thr Ala Phe Pro Ala Asp Ser Asp Arg His Cys Asn Gly Phe Pro Ala
            195                 200                 205

Gly Ala Glu Val Thr Asn Arg Pro Ser Pro Trp Arg Pro Leu Val Leu
210                 215                 220

Leu Ile Pro Leu Arg Leu Gly Leu Thr Asp Ile Asn Glu Ala Tyr Val
225                 230                 235                 240

Glu Thr Leu Lys His Cys Phe Met Met Pro Gln Ser Leu Gly Val Ile
                245                 250                 255

Gly Gly Lys Pro Asn Ser Ala His Tyr Phe Ile Gly Tyr Val Gly Glu
            260                 265                 270

Glu Leu Ile Tyr Leu Asp Pro His Thr Thr Gln Pro Ala Val Glu Pro
        275                 280                 285

Thr Asp Gly Cys Phe Ile Pro Asp Glu Ser Phe His Cys Gln His Pro
    290                 295                 300

Pro Cys Arg Met Ser Ile Ala Glu Leu Asp Pro Ser Ile Ala Val Gly
305                 310                 315                 320

Phe Phe Cys Lys Thr Glu Asp Asp Phe Asn Asp Trp Cys Gln Gln Val
                325                 330                 335

Lys Lys Leu Ser Leu Leu Gly Gly Ala Leu Pro Met Phe Glu Leu Val
            340                 345                 350

Glu Leu Gln Pro Ser His Leu Ala Cys Pro Asp Val Leu Asn Leu Ser
        355                 360                 365

Leu Asp Ser Ser Asp Val Glu Arg Leu Glu Arg Phe Phe Asp Ser Glu
    370                 375                 380

Asp Glu Asp Phe Glu Ile Leu Ser Leu
385                 390

<210> SEQ ID NO 2
<211> LENGTH: 399
<212> TYPE: PRT
<213> ORGANISM: Homo sapiens

<400> SEQUENCE: 2

Met Ala His Ser Val Pro Ser Asp Ser Arg Gly Ser Val Gly Gly Arg
1               5                   10                  15

Thr Gly Lys Met Asp Ala Ala Thr Leu Thr Tyr Asp Thr Leu Arg Phe
            20                  25                  30

Ala Glu Phe Glu Asp Phe Pro Glu Thr Ser Glu Pro Val Trp Ile Leu
        35                  40                  45

-continued

```
Gly Arg Lys Tyr Ser Ile Phe Thr Glu Lys Asp Glu Ile Leu Ser Asp
         50                  55                  60

Val Ala Ser Arg Leu Trp Phe Thr Tyr Arg Lys Asn Phe Pro Ala Ile
 65                  70                  75                  80

Gly Gly Thr Gly Pro Thr Ser Asp Thr Gly Trp Gly Cys Met Leu Arg
                 85                  90                  95

Cys Gly Gln Met Ile Phe Ala Gln Ala Leu Val Cys Arg His Leu Gly
                100                 105                 110

Arg Asp Trp Arg Trp Thr Gln Arg Lys Arg Gln Pro Asp Ser Tyr Phe
            115                 120                 125

Ser Val Leu Asn Ala Phe Ile Asp Arg Lys Asp Ser Tyr Tyr Ser Ile
130                 135                 140

His Gln Ile Ala Gln Met Gly Val Gly Glu Gly Lys Ser Ile Gly Gln
145                 150                 155                 160

Trp Tyr Gly Pro Asn Thr Val Ala Gln Val Leu Lys Lys Leu Ala Val
                165                 170                 175

Phe Asp Thr Trp Ser Ser Leu Ala Val His Ile Ala Met Asp Asn Thr
                180                 185                 190

Val Val Met Glu Glu Ile Arg Arg Leu Cys Arg Thr Ser Val Pro Cys
            195                 200                 205

Ala Gly Ala Thr Ala Phe Pro Ala Asp Ser Asp Arg His Cys Asn Gly
210                 215                 220

Phe Pro Ala Gly Ala Glu Val Thr Asn Arg Pro Ser Pro Trp Arg Pro
225                 230                 235                 240

Leu Val Leu Leu Ile Pro Leu Arg Leu Gly Leu Thr Asp Ile Asn Glu
                245                 250                 255

Ala Tyr Val Glu Thr Leu Lys His Cys Phe Met Met Pro Gln Ser Leu
                260                 265                 270

Gly Val Ile Gly Gly Lys Pro Asn Ser Ala His Tyr Phe Ile Gly Tyr
            275                 280                 285

Val Gly Glu Glu Leu Ile Tyr Leu Asp Pro His Thr Thr Gln Pro Ala
290                 295                 300

Val Glu Pro Thr Asp Gly Cys Phe Ile Pro Asp Glu Ser Phe His Cys
305                 310                 315                 320

Gln His Pro Pro Cys Arg Met Ser Ile Ala Glu Leu Asp Pro Ser Ile
                325                 330                 335

Ala Val Gly Phe Phe Cys Lys Thr Glu Asp Asp Phe Asn Asp Trp Cys
                340                 345                 350

Gln Gln Val Lys Lys Leu Ser Leu Leu Gly Gly Ala Leu Pro Met Phe
            355                 360                 365

Glu Leu Val Glu Leu Gln Pro Ser His Leu Ala Cys Pro Asp Val Leu
370                 375                 380

Asn Leu Ser Leu Gly Glu Ser Cys Gln Val Gln Ile Leu Leu Met
385                 390                 395

<210> SEQ ID NO 3
<211> LENGTH: 280
<212> TYPE: PRT
<213> ORGANISM: Homo sapiens

<400> SEQUENCE: 3

Met Leu Arg Cys Gly Gln Met Ile Phe Ala Gln Ala Leu Val Cys Arg
 1               5                  10                  15

His Leu Gly Arg Asp Trp Arg Trp Thr Gln Arg Lys Arg Gln Pro Asp
                 20                  25                  30
```

```
Ser Tyr Phe Ser Val Leu Asn Ala Phe Ile Asp Arg Lys Asp Ser Tyr
            35                  40                  45

Tyr Ser Ile His Gln Ile Ala Gln Met Gly Val Gly Glu Gly Lys Ser
        50                  55                  60

Ile Gly Gln Trp Tyr Gly Pro Asn Thr Val Ala Gln Val Leu Lys Lys
65                  70                  75                  80

Leu Ala Val Phe Asp Thr Trp Ser Ser Leu Ala Val His Ile Ala Met
                85                  90                  95

Asp Asn Thr Val Val Met Glu Glu Ile Arg Arg Leu Cys Arg Thr Ser
                100                 105                 110

Val Pro Cys Ala Gly Ala Thr Ala Phe Pro Ala Asp Ser Asp Arg His
            115                 120                 125

Cys Asn Gly Phe Pro Ala Gly Ala Glu Val Thr Asn Arg Pro Ser Pro
130                 135                 140

Trp Arg Pro Leu Val Leu Leu Ile Pro Leu Arg Leu Gly Leu Thr Asp
145                 150                 155                 160

Ile Asn Glu Ala Tyr Val Glu Thr Leu Lys His Cys Phe Met Met Pro
                165                 170                 175

Gln Ser Leu Gly Val Ile Gly Gly Lys Pro Asn Ser Ala His Tyr Phe
            180                 185                 190

Ile Gly Tyr Val Gly Glu Glu Leu Ile Tyr Leu Asp Pro His Thr Thr
            195                 200                 205

Gln Pro Ala Val Glu Pro Thr Asp Gly Cys Phe Ile Pro Asp Glu Ser
            210                 215                 220

Phe His Cys Gln His Pro Pro Cys Arg Met Ser Ile Ala Glu Leu Asp
225                 230                 235                 240

Pro Ser Ile Ala Val Gly Lys Gln Gly Arg Leu Val Arg Ser Leu Ile
                245                 250                 255

Pro Trp Ala Pro Arg Pro Ser Ser Trp Cys Ala Ala Val Leu Gly Ala
                260                 265                 270

Ala Val Val Met Cys Gly Thr Pro
            275                 280

<210> SEQ ID NO 4
<211> LENGTH: 331
<212> TYPE: PRT
<213> ORGANISM: Homo sapiens

<400> SEQUENCE: 4

Met Leu Arg Cys Gly Gln Met Ile Phe Ala Gln Ala Leu Val Cys Arg
1               5                   10                  15

His Leu Gly Arg Asp Trp Arg Trp Thr Gln Arg Lys Arg Gln Pro Asp
            20                  25                  30

Ser Tyr Phe Ser Val Leu Asn Ala Phe Ile Asp Arg Lys Asp Ser Tyr
            35                  40                  45

Tyr Ser Ile His Gln Ile Ala Gln Met Gly Val Gly Glu Gly Lys Ser
        50                  55                  60

Ile Gly Gln Trp Tyr Gly Pro Asn Thr Val Ala Gln Val Leu Lys Lys
65                  70                  75                  80

Leu Ala Val Phe Asp Thr Trp Ser Ser Leu Ala Val His Ile Ala Met
                85                  90                  95

Asp Asn Thr Val Val Met Glu Glu Ile Arg Arg Leu Cys Arg Thr Ser
                100                 105                 110

Val Pro Cys Ala Gly Ala Thr Ala Phe Pro Ala Asp Ser Asp Arg His
            115                 120                 125
```

-continued

```
Cys Asn Gly Phe Pro Ala Gly Ala Glu Val Thr Asn Arg Pro Ser Pro
    130                 135                 140

Trp Arg Pro Leu Val Leu Leu Ile Pro Leu Arg Leu Gly Leu Thr Asp
145                 150                 155                 160

Ile Asn Glu Ala Tyr Val Glu Thr Leu Lys His Cys Phe Met Met Pro
                165                 170                 175

Gln Ser Leu Gly Val Ile Gly Gly Lys Pro Asn Ser Ala His Tyr Phe
            180                 185                 190

Ile Gly Tyr Val Gly Glu Glu Leu Ile Tyr Leu Asp Pro His Thr Thr
        195                 200                 205

Gln Pro Ala Val Glu Pro Thr Asp Gly Cys Phe Ile Pro Asp Glu Ser
    210                 215                 220

Phe His Cys Gln His Pro Pro Cys Arg Met Ser Ile Ala Glu Leu Asp
225                 230                 235                 240

Pro Ser Ile Ala Val Gly Phe Phe Cys Lys Thr Glu Asp Asp Phe Asn
                245                 250                 255

Asp Trp Cys Gln Gln Val Lys Lys Leu Ser Leu Leu Gly Gly Ala Leu
            260                 265                 270

Pro Met Phe Glu Leu Val Glu Leu Gln Pro Ser His Leu Gly Glu Ser
        275                 280                 285

Cys Gln Val Gln Val Gly Ser Leu Gly Ala Cys Pro Asp Val Leu Asn
    290                 295                 300

Leu Ser Leu Asp Ser Ser Asp Val Glu Arg Leu Glu Arg Phe Phe Asp
305                 310                 315                 320

Ser Glu Asp Glu Asp Phe Glu Ile Leu Ser Leu
                325                 330

<210> SEQ ID NO 5
<211> LENGTH: 331
<212> TYPE: PRT
<213> ORGANISM: Homo sapiens

<400> SEQUENCE: 5

Met Leu Arg Cys Gly Gln Met Ile Phe Ala Gln Ala Leu Val Cys Arg
1               5                   10                  15

His Leu Gly Arg Asp Trp Arg Trp Thr Gln Arg Lys Arg Gln Pro Asp
            20                  25                  30

Ser Tyr Phe Ser Val Leu Asn Ala Phe Ile Asp Arg Lys Asp Ser Tyr
        35                  40                  45

Tyr Ser Ile His Gln Ile Ala Gln Met Gly Val Gly Glu Gly Lys Ser
    50                  55                  60

Ile Gly Gln Trp Tyr Gly Pro Asn Thr Val Ala Gln Val Leu Lys Lys
65                  70                  75                  80

Leu Ala Val Phe Asp Thr Trp Ser Ser Leu Ala Val His Ile Ala Met
                85                  90                  95

Asp Asn Thr Val Val Met Glu Glu Ile Arg Arg Leu Cys Arg Thr Ser
            100                 105                 110

Val Pro Cys Ala Gly Ala Thr Ala Phe Pro Ala Asp Ser Asp Arg His
        115                 120                 125

Cys Asn Gly Phe Pro Ala Gly Ala Glu Val Thr Asn Arg Pro Ser Pro
    130                 135                 140

Trp Arg Pro Leu Val Leu Leu Ile Pro Leu Arg Leu Gly Leu Thr Asp
145                 150                 155                 160

Ile Asn Glu Ala Tyr Val Glu Thr Leu Lys His Cys Phe Met Met Pro
                165                 170                 175
```

```
Gln Ser Leu Gly Val Ile Gly Gly Lys Pro Asn Ser Ala His Tyr Phe
            180             185                 190

Ile Gly Tyr Val Gly Glu Glu Leu Ile Tyr Leu Asp Pro His Thr Thr
        195             200                 205

Gln Pro Ala Val Glu Pro Thr Asp Gly Cys Phe Ile Pro Asp Glu Ser
    210             215                 220

Phe His Cys Gln His Pro Pro Cys Arg Met Ser Ile Ala Glu Leu Asp
225             230                 235                 240

Pro Ser Ile Ala Val Gly Phe Phe Cys Lys Thr Glu Asp Asp Phe Asn
            245             250                 255

Asp Trp Cys Gln Gln Val Lys Lys Leu Ser Leu Leu Gly Gly Ala Leu
            260             265                 270

Pro Met Phe Glu Leu Val Glu Leu Gln Pro Ser His Leu Gly Glu Ser
        275             280                 285

Cys Gln Val Gln Val Gly Ser Leu Gly Ala Cys Pro Asp Val Leu Asn
    290             295                 300

Leu Ser Leu Asp Ser Ser Asp Val Glu Arg Leu Glu Arg Phe Phe Asp
305             310                 315                 320

Ser Glu Asp Glu Asp Phe Glu Ile Leu Ser Leu
            325             330
```